United States Patent
Hsu et al.

(10) Patent No.: US 10,416,031 B2
(45) Date of Patent: Sep. 17, 2019

(54) PRESSURE SENSING DEVICE

(71) Applicant: MedicusTek, Inc., Taipei (TW)

(72) Inventors: Chia-Ming Hsu, Taipei (TW); Chung-Chih Lin, Taipei (TW); Chi Wen Liu, Taipei (TW); Chun Lin, Taipei (TW); Chao-Hung Chou, Taipei (TW)

(73) Assignee: MedicusTek, Inc., Taipei (TW)

( * ) Notice: Subject to any disclaimer, the term of this patent is extended or adjusted under 35 U.S.C. 154(b) by 815 days.

(21) Appl. No.: 14/866,076

(22) Filed: Sep. 25, 2015

(65) Prior Publication Data

US 2017/0089775 A1    Mar. 30, 2017

(51) Int. Cl.
| | |
|---|---|
| *G01L 1/16* | (2006.01) |
| *A61B 5/00* | (2006.01) |
| *A61B 5/103* | (2006.01) |
| *A61G 7/05* | (2006.01) |
| *A61B 5/11* | (2006.01) |
| *A61B 5/0205* | (2006.01) |
| *A61B 5/113* | (2006.01) |

(52) U.S. Cl.
CPC .............. *G01L 1/16* (2013.01); *A61B 5/1036* (2013.01); *A61B 5/6892* (2013.01); *A61G 7/05* (2013.01); *A61B 5/02055* (2013.01); *A61B 5/1102* (2013.01); *A61B 5/113* (2013.01); *A61B 5/1116* (2013.01); *A61B 2562/0247* (2013.01); *A61B 2562/046* (2013.01); *A61G 2203/30* (2013.01); *A61G 2203/34* (2013.01); *A61G 2203/36* (2013.01)

(58) Field of Classification Search
CPC ........... G01L 1/16; G01L 1/14; A61B 5/6892; A61B 5/1036; A61B 5/02055; A61B 5/1102; A61B 2562/046; A61B 2562/0247; A61B 5/113; A61B 5/1116; A61G 7/05; A61G 2203/36; A61G 2203/30; A61G 2203/34
See application file for complete search history.

(56) References Cited

U.S. PATENT DOCUMENTS

| | | | | |
|---|---|---|---|---|
| 4,634,917 A | * | 1/1987 | Dvorsky | G01B 7/004 310/323.21 |
| 4,985,952 A | * | 1/1991 | Edelson | A47C 27/001 150/158 |
| 6,990,176 B2 | * | 1/2006 | Sherman | A61B 6/032 250/370.09 |
| 8,510,878 B2 | * | 8/2013 | Wang | A47G 27/0237 5/417 |

(Continued)

*Primary Examiner* — Nicholas F Polito
*Assistant Examiner* — Alexis Felix Lopez
(74) *Attorney, Agent, or Firm* — Osha Liang LLP

(57) ABSTRACT

A pressure sensing mat may include: a first substrate; a second substrate disposed opposite to the first substrate; a first electrode layer disposed on a side of the first substrate that faces the second substrate, the first electrode layer comprising a plurality of first electrode patterns; a second electrode layer disposed on a side of the second substrate that faces the first substrate, the second electrode layer comprising a plurality of second electrode patterns; and a spacer layer disposed between the first substrate and the second substrate and comprising a plurality of holes such that the first electrode patterns are configured to contact the second electrode patterns through the holes.

23 Claims, 19 Drawing Sheets

(56) References Cited

U.S. PATENT DOCUMENTS

| | | | | |
|---|---|---|---|---|
| 8,661,915 B2* | 3/2014 | Taylor | ............... | G01L 1/18 |
| | | | | 73/862.044 |
| 8,922,225 B2* | 12/2014 | Chiou | ............... | A61B 5/6892 |
| | | | | 200/85 R |
| 9,282,893 B2* | 3/2016 | Longinotti-Buitoni | ............... | |
| | | | | A61B 5/6804 |
| 2008/0097250 A1* | 4/2008 | Tochigi | ............... | A61B 5/024 |
| | | | | 600/595 |
| 2010/0253183 A1* | 10/2010 | Ando | ............... | G01L 1/16 |
| | | | | 310/338 |
| 2012/0041345 A1* | 2/2012 | Rajamani | ............... | A61B 5/103 |
| | | | | 600/587 |
| 2013/0197387 A1* | 8/2013 | Lipoma | ............... | A61B 5/0004 |
| | | | | 600/535 |
| 2014/0084045 A1* | 3/2014 | Yang | ............... | G06F 19/00 |
| | | | | 228/175 |
| 2014/0090489 A1* | 4/2014 | Taylor | ............... | G01L 1/00 |
| | | | | 73/862.626 |
| 2014/0373594 A1* | 12/2014 | Remez | ............... | G01L 25/00 |
| | | | | 73/1.08 |
| 2015/0049330 A1* | 2/2015 | Aliane | ............... | G06F 3/0414 |
| | | | | 356/72 |
| 2016/0327441 A1* | 11/2016 | Iwase | ............... | A61B 5/1036 |

* cited by examiner

PRESSURE SENSING DEVICE

BACKGROUND

There is a strong demand in the health care industry for medical devices that facilitate the timely, cost effective, and efficient means of treating patients. Medical devices that are able to provide the above advantages over currently employed practices may allow for the health care providers and the health care recipients to both lessen their costs and increase their quality of care through the rapid detection of potential problems before more intensive intervention and treatment is necessary.

In a health care setting (e.g., a hospital, recovery facility, home-health environment, etc.) the patient may spend a large portion of their time unaccompanied in their bed within their room. While the health care staff may routinely physically check in on the patient's well-being, due to the presence of a multitude of patients for every staff member, the rapid detection of potential problems may be lacking. In these situations the ability to remotely collect data regarding the condition of each patient may prove beneficial to their care.

Accordingly, there exists a need for medical devices capable of collecting data regarding aspects of a patient's condition, transmitting said data to health care professionals, and potentially alerting health care professionals if rapid intervention is necessary.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a pressure sensing mat that includes: a first substrate; a second substrate disposed opposite to the first substrate; a first electrode layer disposed on a side of the first substrate that faces the second substrate, the first electrode layer comprising a plurality of first electrode patterns; a second electrode layer disposed on a side of the second substrate that faces the first substrate, the second electrode layer comprising a plurality of second electrode patterns; and a spacer layer disposed between the first substrate and the second substrate and comprising a plurality of holes such that the first electrode patterns are configured to contact the second electrode patterns through the holes.

In another aspect, embodiments disclosed herein relate to a mattress that includes: at least two layers of a foamed polymeric material; a pressure sensing mat disposed between the at least two layers of a foamed polymeric material, the pressure sensing mat including: a first substrate; a second substrate disposed opposite to the first substrate; a first electrode layer disposed on a side of the first substrate that faces the second substrate, the first electrode layer comprising a plurality of first electrode patterns; a second electrode layer disposed on a side of the second substrate that faces the first substrate, the second electrode layer comprising a plurality of second electrode patterns; and a spacer layer disposed between the first substrate and the second substrate and comprising a plurality of holes such that the first electrode patterns are configured to contact the second electrode patterns through the holes.

In yet another aspect, embodiments disclosed herein relate to a pressure sensing device that includes: at least one piezoelectric module; a pressure sensing mat disposed adjacent to the surface of the at least one piezoelectric module; and the at least one piezoelectric module and the pressure sensing mat configured to connect to a processor.

DETAILED DESCRIPTION

Figure 1:
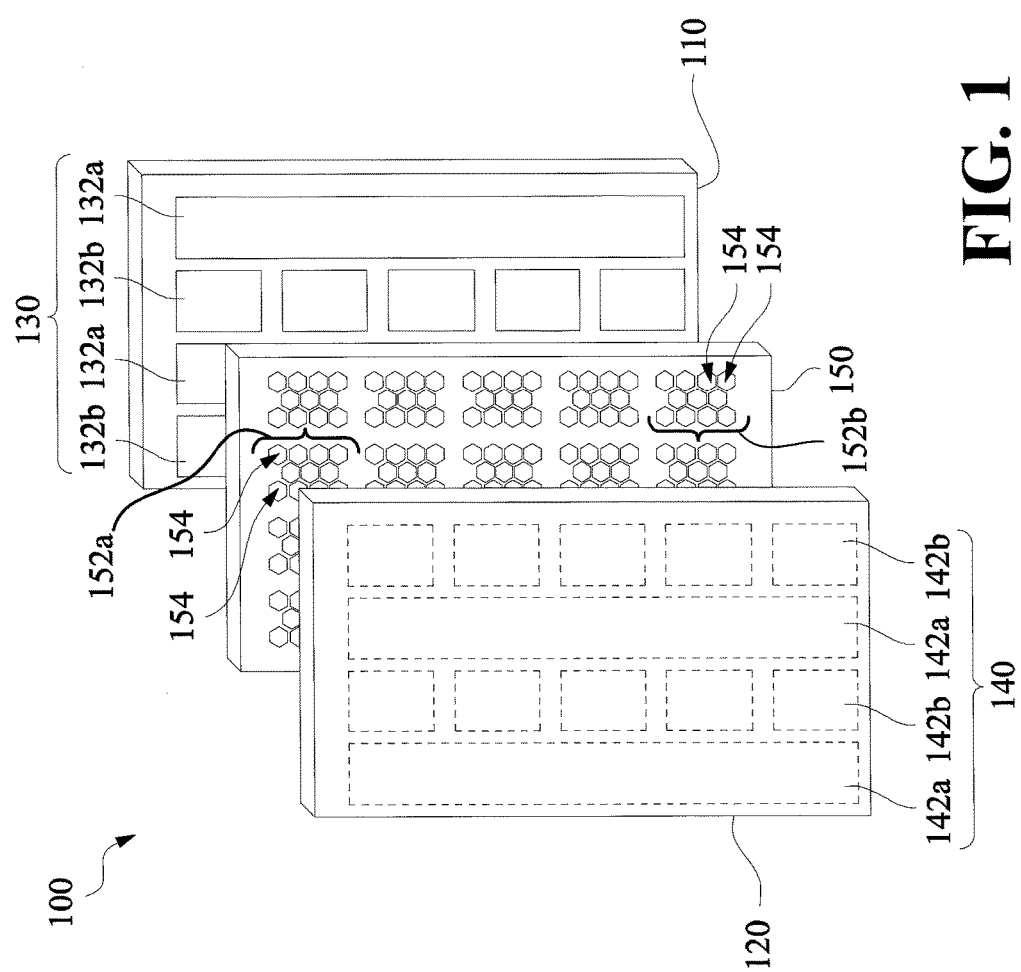
FIG. 1 shows a pressure sensing mat according to one or more embodiments of the present disclosure.

The medical device field would be greatly enhanced by medical instruments which are able to monitor the posture, breathing rhythm, heartbeat, pulse, body temperature and other actions of a patient when on a bed so as to provide timely and efficient care. For example, when a patient has a medical episode such as an epileptic seizure, or is otherwise at risk of falling out of the bed, the timely intervention by health care professionals aided by a medical instrument capable of prompt notification of the potentially dangerous situation can significantly mitigate the chances of damage and harm to the patient.

Further, a long term analysis of changes in the posture, breathing rhythm, and other actions of a patient while in the bed may facilitate the detection of underlying health conditions and reactions to prescribed medications. For example, such changes can inform a medical practitioner about the patient's sleep patterns, amount of activity, body movements reflecting physical pain, and the susceptibility to bedsore due to lack of movement. Understanding these non-verbal signals produced by the body may be particularly beneficial to patients who have difficulties communicating with the health care professionals and nursing staff.

In general, to promote wide adoption and maximize the benefits described above, such a medical device may have a simple cost effective construction that is amenable to mass production, while capable of being integrated into soft structures so that the device is not noticeable or uncomfortable. In some embodiments, devices of the present application may be utilized in a wearable device.

One or more embodiments of the present disclosure generally relate to a pressure sensing device. Further, one or more embodiments of the present disclosure relate to a pressure sensing mat and its potential application in sensing various conditions of a patient. Specific embodiments will now be described in detail with reference to the accompanying figures. Like elements in the various figures may be denoted by like reference numerals for consistency. Like elements may not be labeled in all figures for the sake of simplicity.

In the following detailed description, numerous specific details are set forth in order to provide a more thorough understanding of one or more embodiments of the present invention. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create a particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and follow (or precede) the second element in an ordering of elements.

It is to be understood that the singular forms "a," "an," and "the" include plural referents unless the context clearly dictates otherwise. Thus, for example, reference to "a component surface" includes reference to one or more of such surfaces.

Terms like "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Pressure Sensing Mat

FIG. 1 shows a pressure sensing mat 100 according to one or more embodiments of the present invention. The pressure sensing mat 100 comprises a first substrate 110, a second substrate 120, a first electrode layer 130, a second electrode layer 140, and a spacer layer 150. The second substrate 120 is disposed opposite to the first substrate 110. The first electrode layer 130 is disposed on a side of the first substrate 110 that faces the second substrate 120, and the first electrode layer 130 comprises a plurality of first electrode patterns 132a, 132b. The second electrode layer 140 is disposed on a side of the second substrate 120 that faces the first substrate 110, and the second electrode layer 140 comprises a plurality of second electrode patterns 142a, 142b. The spacer layer 150 is disposed between the first electrode layer 130 and the second electrode layer 140, and comprises a plurality of holes 154 connecting each side of the spacer layer 150 such that when a user exerts pressure on a specific location of the first substrate 110 or the second substrate 120, the first electrode patterns 132a, 132b in the specific location where the pressure is exerted is configured to contact the corresponding second electrode patterns 142b, 142a via the holes 154 of the spacer layer 150 in the specific location where the pressure is exerted.

Although FIG. 1 shows that the first electrode layer 130 and the second electrode layer 140 have square electrode patterns 132b, 142b and rectangular electrode patterns 132a, 142a. The electrode patterns of the first electrode layer 130 and the second electrode layer 140 are actually disposed within the square and rectangular grids. Specifically, the square and rectangular grids themselves are not the electrode patterns and are only labeled to show the boundaries of the substrate areas including the electrode patterns for the convenience of the description. Further, in FIG. 1, the first electrode layer 130 is drawn with solid lines and the second electrode layer 140 is drawn with dotted lines because the first electrode layer 130 can be observed directly while the second electrode layer 140 is drawn facing into the page and cannot be directly observed.

In one or more embodiments of the present invention, the first electrode patterns 132b (as one example of a plurality of the first electrode patterns in the square grids shown in FIG. 1) is disposed to face the second electrode patterns 142a and the second electrode patterns 142b (as one example of a plurality of the second electrode patterns in the square grids shown in FIG. 1) is disposed to face the first electrode patterns 132a. In particular, the electrode patterns are disposed such that electrodes in the square grids are configured to contact electrodes in the rectangular grids. In FIG. 1, the electrodes in the ten square grids of the first electrode layer 130 comprising the first electrode patterns 132b are configured to contact the second electrode patterns 142a. Similarly, the electrodes in the ten square grids of the second electrode layer 140 comprising the second electrode patterns 142b are configured to contact the first electrode patterns 132a. In one or more embodiments of the present invention, the first electrode patterns 132a and the second electrode patterns 142a may be grounding electrodes. In one or more embodiments of the present invention, the first electrode patterns 132b and the second electrode patterns 142b may be conducting electrodes. According to FIG. 1, a grounding electrode may be configured to contact a plurality of conducting electrodes.

Though the first electrode patterns 132a, 132b and the second electrode patterns 142a, 142b are indicated as arranged in rectangular grids and square grids, one of ordinary skill in the art would appreciate that the electrode patterns may be organized to be in grids in hexagonal, circular or other desirable shape. Further, one of ordinary skill in the art would appreciate that the particular circuitry configuration, number, size, etc., of the first electrode patterns 132a, 132b and the second electrode patterns 142a, 142b can vary without departing from the scope of the present invention.

In one or more embodiments of the present invention, the spacer layer 150 comprises a plurality of hole patterns with 152a and 152b being examples shown in FIG. 1. Each hole pattern 152a or 152b comprises a plurality of holes 154 (as example shown in FIG. 1). The hole patterns 152a are disposed to coincide with a corresponding portion of the first electrode patterns 132b on one side and the second electrode patterns 142a on the other side; the hole patterns 152b are disposed to coincide with a corresponding portion of the first electrode patterns 132a on one side and the second electrode patterns 142b on the other side. As shown in FIG. 1, the first electrode patterns 132a are configured to contact the hole patterns 152b, whereas each of the first electrode patterns 132b is configured to contact only one hole pattern 152a.

Though the holes 154 are shown in FIG. 1 to be hexagonal in shape, one of ordinary skill in the art would appreciate that the holes 154 may be square or circular in shape without departing from the scope of the present invention. Similarly, the number, size, configuration, etc., of the hole patterns 152a and 152b or the holes 154 shown in FIG. 1 can vary without departing from the scope of the present invention. It is through these holes 154 that the electrode patterns disposed opposing each other on the first substrate 110 and the second substrate 120 will touch upon the application of a threshold pressure, thereby registering a signal due to the grounding of formerly conducting electrodes (132b and 142b).

Figure 21:
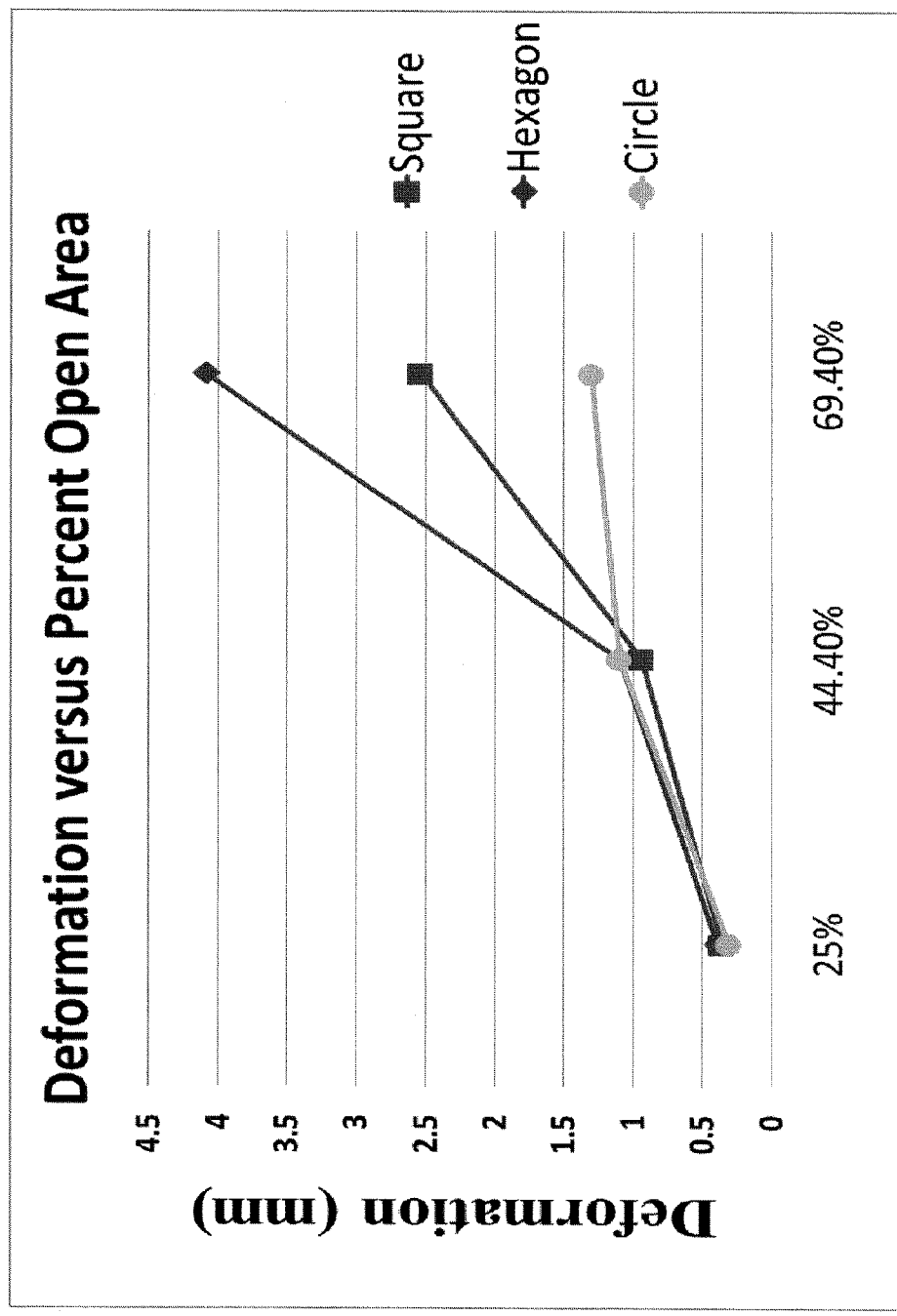
FIG. 21 shows experimental data on the deformation characteristics of different hole shapes according to some embodiments.

Hexagonally shaped holes according to one or more embodiments of the invention have been shown in experiments to be sensitive and, therefore, advantageous. FIG. 21 depicts results from an experimental study on the deformation characteristics of different hole shapes. In the experiment a 50 g weight was placed on a spacer layer having either square, hexagonal, or circular holes thereon. The deformation (in mm) of the spacer layer was measured for each different shape and also when using each shape with different sizes of hole openings (e.g., larger openings equal a larger percent "open" area within the spacer layer). The results shown in FIG. 21 illustrate that, while hole shape does not really change deformation up to certain hole sizes, hexagonal holes have significantly more deformation as the hole size becomes larger (i.e., increase in percent open area). The increase in deformation for hexagonal holes may be useful to increase the sensitivity of a pressure sensing device because ultimately the spacer layer must deform under pressure in order to register a signal by the electrodes contacting each other. Thus, FIG. 21 illustrates that by modulating the shape and size of the holes in the spacer layer one may tune the critical force or pressure required to deform a spacer layer of specific thickness so that a signal may be registered in response to a range of expected forces or pressures.

In one or more embodiments of the present invention, the pressure sensing mat 100 detects a pressure exerted on the first electrode patterns 132a, 132b or the second electrode patterns 142a, 142b through the hole patterns 152a, 152b. The shapes of the hole patterns 152a, 152b are arranged to substantially match the first electrode patterns 132a, 132b and the second electrode patterns 142a, 142b. For example, in FIG. 1, the hole patterns 152a, 152b are substantially square in shape; that is, the holes 154 are arranged in the square to match the square and rectangular grid where the electrode patterns 132a, 132b, 142a, 142b are arranged. If the first electrode patterns 132a, 132b and the second electrode patterns 142a, 142b are arranged in some other shapes of grids, the shapes of the hole patterns may be adjusted accordingly.

In one or more embodiments of the present embodiment, a thickness of the spacer layer 150 may be adjusted based on a user's attributes (e.g., weight). For example, the spacer layer 150 of the pressure sensing mat 100 designed for adult males may be thicker than spacer layers designed for adult females, which, in turn, may be thicker than ones designed for juveniles. In particular, the weight of the user may affect the pressure sensitivity of the pressure sensing mat 100. For example, the discussion and considerations presented above regarding what is shown by FIG. 21 may be used to create tailored pressure mats for various individuals by tuning at least one of the spacer thickness, hole size, and hole shape.

In one or more embodiments of the present invention, the first substrate 110 and the second substrate 120 may be made of flexible films, the materials of which may be one independently selected from the group consisting of: polyethylene terephthalate (PET), thermoplastic polyurethane (TPU), other plastics, other flexible materials, and combinations thereof. Further, the material of the first substrate 110 or the second substrate 120 may be cloth or some other soft material, such as cotton, flax wool, ramie, silk, leather and fur etc. that can minimize noise as well as enhance comfort level when the user interacts with the first substrate 110 or the second substrate 120. In one or more embodiments of the present invention, the thickness of the first substrate 110 and the second substrate 120 may be 1.4 μm or more.

In one or more embodiments of the present invention, the spacer layer 150 is a flexible and deformable insulating material, which may be one selected from the group consisting of polyethylene terephthalate (PET), thermoplastic polyurethane (TPU), synthetic or natural sponge, foamed plastics, and combinations thereof. In one or more embodiments of the present invention, the thickness of the spacer layer 150 may be 3 mm or more.

Figure 2:
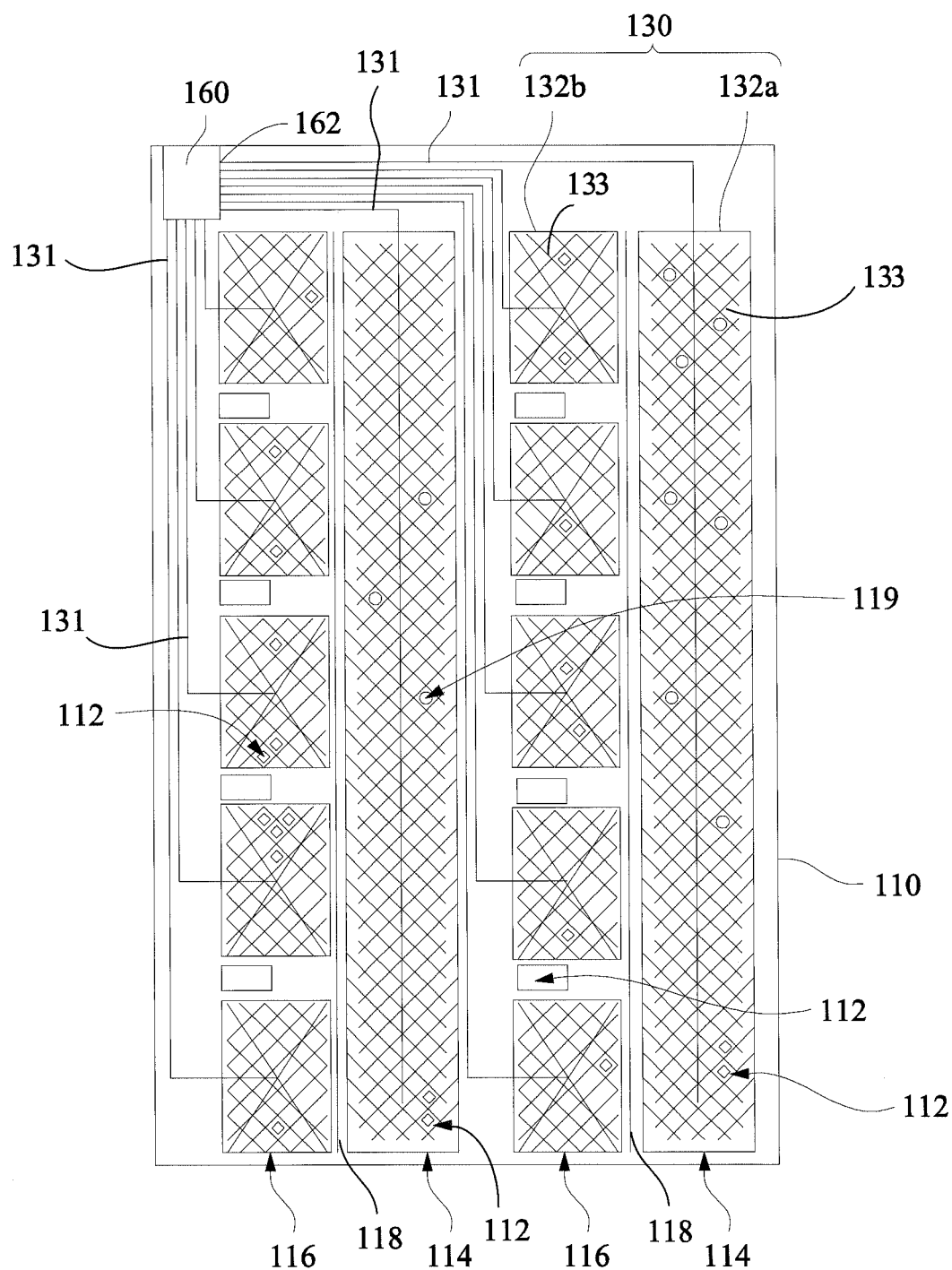
FIG. 2 shows a view of a substrate of a pressure sensing mat showing more details of the electrode layer according to one or more embodiments of the present disclosure.

FIG. 2 shows a more detailed view of a substrate of a pressure sensing mat according to one or more embodiments of the present invention. In this view more detail of the wiring and configuration of the electrode patterns is shown. As shown in FIG. 2, the first electrode layer 130 comprises a plurality of main wires 131, a plurality of subsidiary wires 133, and the first electrode patterns 132a, 132b (and also the other rectangular and square electrode patters that are not labeled for the convenience of the illustration). Further, the pressure sensing mat 100 comprises a processor 160 that is operatively connected to the electrode patterns by the plurality of main wires 131. Similarly, in one or more embodiments of the present invention, the second electrode layer 140 of the second substrate 120 also comprises a plurality of main wires, a plurality of subsidiary wires, and the second electrode patterns 142a, 142b. The main wires of the second substrate 120 operatively connect the second electrode patterns 142a, 142b and the processor 160 disposed on the first substrate 110.

Figure 3A:
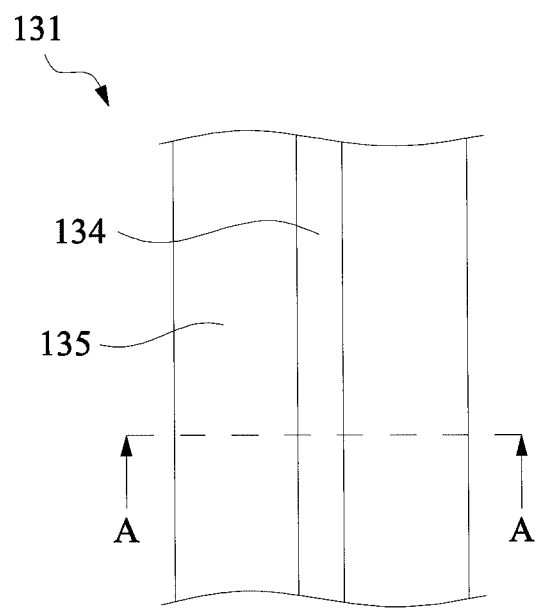
FIG. 3A shows a top view of a main wire of a pressure sensing mat according to one or more embodiments of the present disclosure.
Figure 3B:
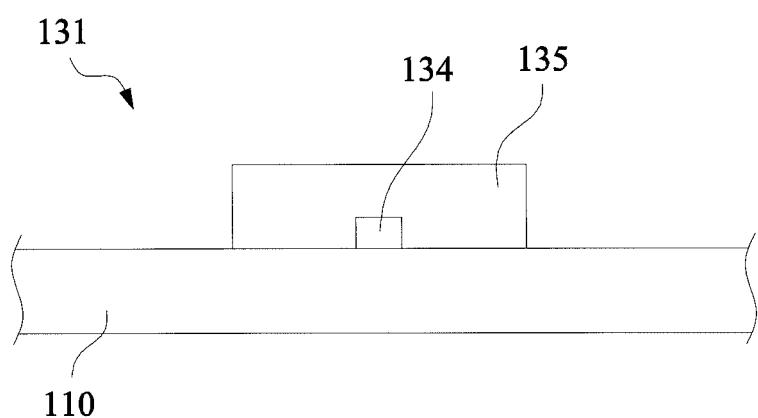
FIG. 3B shows a sectional view of the main wire shown in FIG. 3A along line A-A.

FIG. 3A shows a top view of a main wire of a pressure sensing mat according to one or more embodiments of the present invention. FIG. 3B shows a sectional view of the main wire shown in FIG. 3A along line A-A.

FIGS. 2, 3A, and 3B are now discussed in combination. In one or more embodiments of the present invention, the first electrode layer 130 comprises the first electrode patterns 132a, 132b. The first electrode patterns 132a, 132b consists of a plurality of the main wires 131 and a plurality of the subsidiary wires 133. The main wires 131 comprise a small area conducting layer 134 and a large area conducting layer 135. In one or more embodiments of the present invention, the large area conducting layer 135 is disposed on and adhered to the small area conducting layer 134, that is the large area conducting layer 135 envelops the small area conducting layer 134. In a non-limiting attempt to define the terms "small area conducting layer" and "large area conducting layer," the small area conducting layer 134 is comparatively smaller in surface area than the large area conducting layer 135. The relatively smaller amount of surface area for the small area conducting layer 134 versus the large area conducting layer 135 can be seen in FIGS. 3A-3B. Further, the large area conducting layer 135 may completely cover the small area conducting layer 134 such that the small area conducting layer 134 is not exposed. The main wires 131 operatively connect the first electrode patterns 132a, 132b to the processor 160. In one or more embodiments of the present invention, the large area conducting layers 135 of the main wires are operatively connected to a plurality of pins 162 of the processor 160. In one or more embodiments, the processor 160 may be unattached to the substrate or pressure sensing mat to allow for the simple and easy replacement of the pressure sensing mat in the event that the mat is damaged or its performance deteriorates. In one or more embodiments, the processor 160 may be arranged outside the substrate or pressure sensing mat and may be operatively connected to the pressure sensing mat or substrate via wiring or cables with an adapter configured to connect the main lines to the processor.

In one or more embodiments of the present invention, the material of the large area conducting layer 135 may be different from that of the small area conducting layer 134. For example, the material of the large area conducting layer 135 may be a conductive ink, whereas the material of the small area conducting layer 134 may be a conductive metal. Superior adhesion and conductivity may be achieved when the material of the large area conducting layer 135 is different from the material of the small area conducting layer 134. In some embodiments, the material of the large area conducting layer may be a conductive carbon-based ink, while the material of the small area conducting layer may be silver metal or alloys thereof. In some embodiments, the small area layer may be a silver wire printed on the substrate while the large area layer may be printed with carbon-based ink covering the silver wire. Of course, one of ordinary skill in the art would appreciate that it is also possible that the material of the large conducting layer 135 is the same as that of the small area conducting layer 134, so long as the product is able to maintain its intended functions.

In one or more embodiments of the present invention, although the large area conducting layer 135 may better adhere to the first substrate 110 than the small area conducting layer 134, the conductivity of the small area conducting layer 134 may, in turn, be greater than that of the large area conducting layer 135. By allowing the large area conducting layer 135 to envelop the small area conducting layer 134 as shown in FIG. 3B, the combination (i.e., the combination of the large area conducting layer 135 and the small area conducting layer 134) achieves both—that is, the combination is able to better adhere to the first substrate 110 than the small area conducting layer 134 would alone and able to provide better conductivity than the large area conducting layer 135 would alone.

Returning to FIG. 2, the first substrate 110 may comprise a plurality of openings 112 to reduce audible noise (this will be explained in further detail later). The first substrate 110 comprises a plurality of grounding areas 114 and a plurality of conducting areas 116. In FIG. 2, the first electrode patterns 132a are grounding electrodes, whereas the first electrode patterns 132b are conducting electrodes. The first electrode patterns 132a are each disposed in the grounding areas 114; and, the first electrode patterns 132b are each disposed in the conducting areas 116. In one or more embodiments of the present invention, the openings 112 are disposed in or around the conducting areas 116 and the grounding areas 114. Any openings 112 present in the conducting areas 116 and the grounding areas 114 are not connected to any electrode patterns and do not interfere with the circuitry configurations or operation of the pressure sensing mat 100. Further, the openings 112 can be in any shape and size. The shape and size of the openings 112 may be adjusted according to the first electrode patterns 132b, 132a to obtain a larger overall area of the openings 112, so as to further reduce audible noise from the substrate made by physical movements of a user.

In one or more embodiments of the present invention, the first substrate 110 comprises a plurality of separation slots 118. The separation slot 118 may be a stretching opening within the substrate that helps reduce audible noise (this will be explained in further detail later). The separation slots 118 may extend all the way through the substrate. In particular, as shown in FIG. 2, the separation slots 118 separate the first substrate 110 into a plurality of sections (not labeled but effectively left, middle, and right sections), with each section of the substrate remaining connected to each other to maintain a contiguous substrate. Advantageously, the combination of openings 112 and the separation slots 118 within the substrates 110 and 120 help reduce audible noise made by any physical movements by a user that may made on the pressure sensing mat when in operation. Similar to the openings 112, the separation slots 118 are not connected to any electrode patterns and do not interfere with the circuitry configuration or operation of the pressure sensing mat 100.

In one or more embodiments of the present invention, the first substrate 110 and the second substrate 120 comprise a plurality of positioning indexes 119. The positioning indexes 119 may be disposed in the grounding areas 114. However, the present invention is not limited thereto. In one or more embodiments of the present invention, the positioning indexes 119 may be disposed in any area other than the conducting areas 116. Referring to both FIGS. 1 and 2, the spacer layer 150 may also comprise a plurality of positioning holes (not shown). In order to fix the first substrate, second substrate, and spacer layer together, the positioning indexes 119 of the first substrate, the corresponding positioning indexes of the second substrate 120 and the corresponding positioning holes of the spacer layer 150 may be aligned. The positioning indexes 119 of the first substrate and the corresponding positioning indexes of the second substrate 120 may be connected together through the corresponding positioning holes of the spacer layer 150 by placing a water proof glue or adhesive and hot pressing (e.g., high frequency or ultrasonic wave welding) the components. One of ordinary skill in the art would appreciate that, although various indexes are shown in the figures to be disposed at certain locations, the actual position, number, size, etc., of the indexes or holes can vary without departing from the scope of the present invention.

In one or more embodiments of the present invention, the second substrate 120, similar to the first substrate 110, may also comprise openings, positioning indexes, separation slots, large area conducting layers, small area conducting layers, etc. One of the differences between the first substrate 110 and the second substrate 120 lies in the electrode patterns. In particular, returning to FIG. 1, the second electrode patterns 142*a* are grounding electrodes and the second electrode patterns 142*b* are conducting electrodes. To achieve better sensitivity, the second electrode patterns 142*a* of the second electrode layer 140 are disposed to coincide with the first electrode patterns 132*b* of the first electrode layer 130, while the second electrode patterns 142*b* of the second electrode layer 140 are disposed to coincide with the first electrode patterns 132*a* of the first electrode layer 130.

Figure 4:
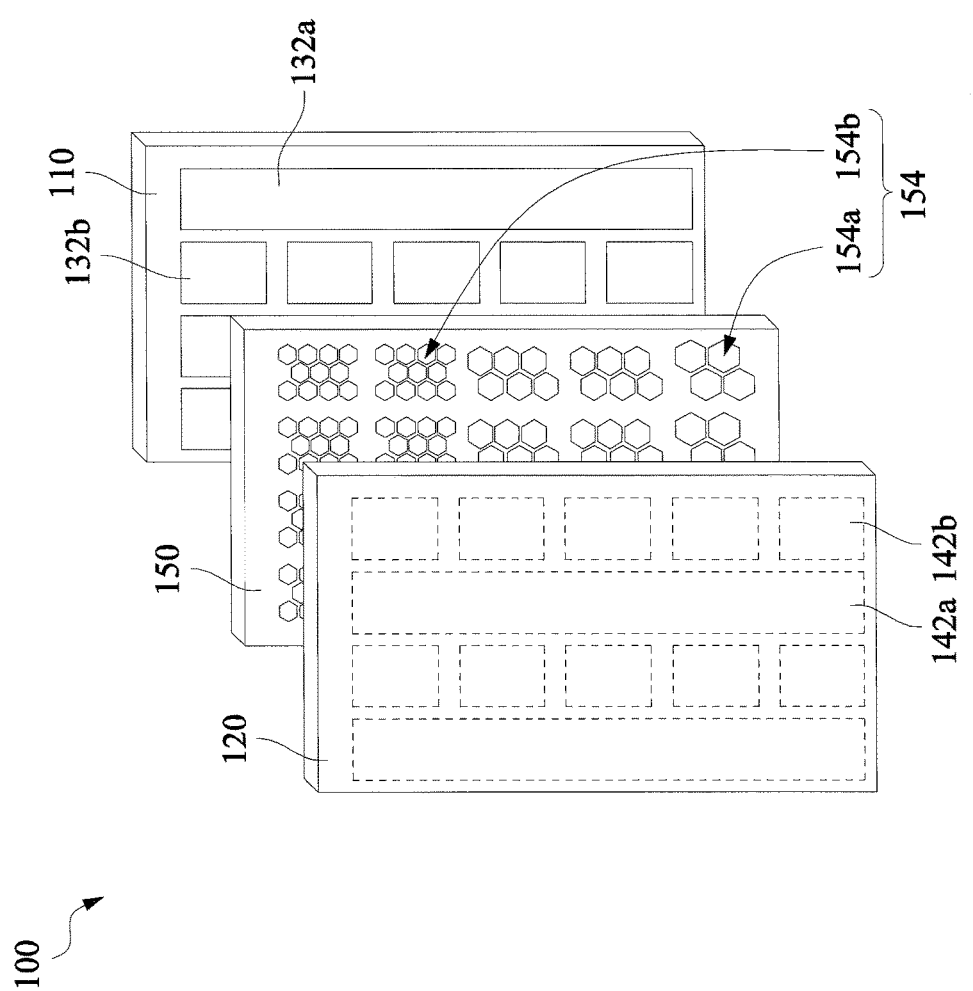
FIG. 4 shows a pressure sensing mat according to one or more embodiments of the present disclosure.

FIG. 4 shows a pressure sensing mat according to one or more embodiments of the present invention. The pressure sensing mat described with respect to FIG. 4 is substantially similar to that shown in FIG. 1. Accordingly, components and functions that have already been described will be omitted for the sake of brevity.

One of the differences between the pressure sensing mat shown in FIG. 1 and the pressure sensing mat shown in FIG. 4 is that, in FIG. 4, the sizes of the holes 154*a*, 154*b* of the spacer layer 150 are not consistent throughout the spacer layer 150. Whereas the holes 154*b* are more in number, the holes 154*a* are larger in size. Of course, as discussed above, the configuration, size, number, placement, etc., of the holes 154 can vary to be compatible with the user's various body parts without departing from the scope of the present invention. For example, large holes 154*a* may provide better sensitivity for coinciding the first electrode patterns 132*a*, 132*b* and the corresponding second electrode patterns 142*b*, 142*a*, while small holes 154*b*, to the contrary, provide lower sensitivity. Thus, the area of the pressure sensitive mat 100 with larger holes 154*a* require less pressure for the electrode patterns to touch and generate a signal, while the area of the pressure sensitive mat 100 with small holes 154*b* requires more pressure for the electrode patterns to touch and generate a signal.

For example, consider a scenario in which a human lies on the pressure sensing mat 100 shown in FIG. 4 with his or her head disposed closer to a top (as depicted in FIG. 4) of the pressure sensing mat 100 than to a bottom of the pressure sensing mat and his or her feet disposed closer to the bottom of the pressure sensing mat than to the top of the pressure sensing mat 100 (i.e., the head is disposed on or close to the small holes 154*b* and the feet are disposed on or close to the large holes 154*a*). As the feet, in comparison to the rest of the body, are relatively small in size (i.e., smaller surface area and weight) and, consequently, exert smaller pressure on the pressure sensing mat 100, the large holes 154*a* are provided to increase sensitivity of feet movement. In comparison, because a torso of the human is relatively heavier and occupies a relatively large area to assert a greater pressure on the pressure sensing mat 100, the smaller holes 154*b* may be adequate to detect any movement of the torso.

Accordingly, the pressure sensing mat 100 may have different sensitivities at different locations according to the different arrangement, shapes, and/or sizes of the holes. The allocation and size of the holes can be arbitrary or can be arranged to match corresponding to human body parts. As discussed above, configurations of the pressure sensing mat are not limited to that shown in FIG. 4. That is, one of ordinary skill in the art would appreciate that the size, shape, number, location, etc., of the holes 154 can vary without departing from the scope of the present invention.

Figure 5:
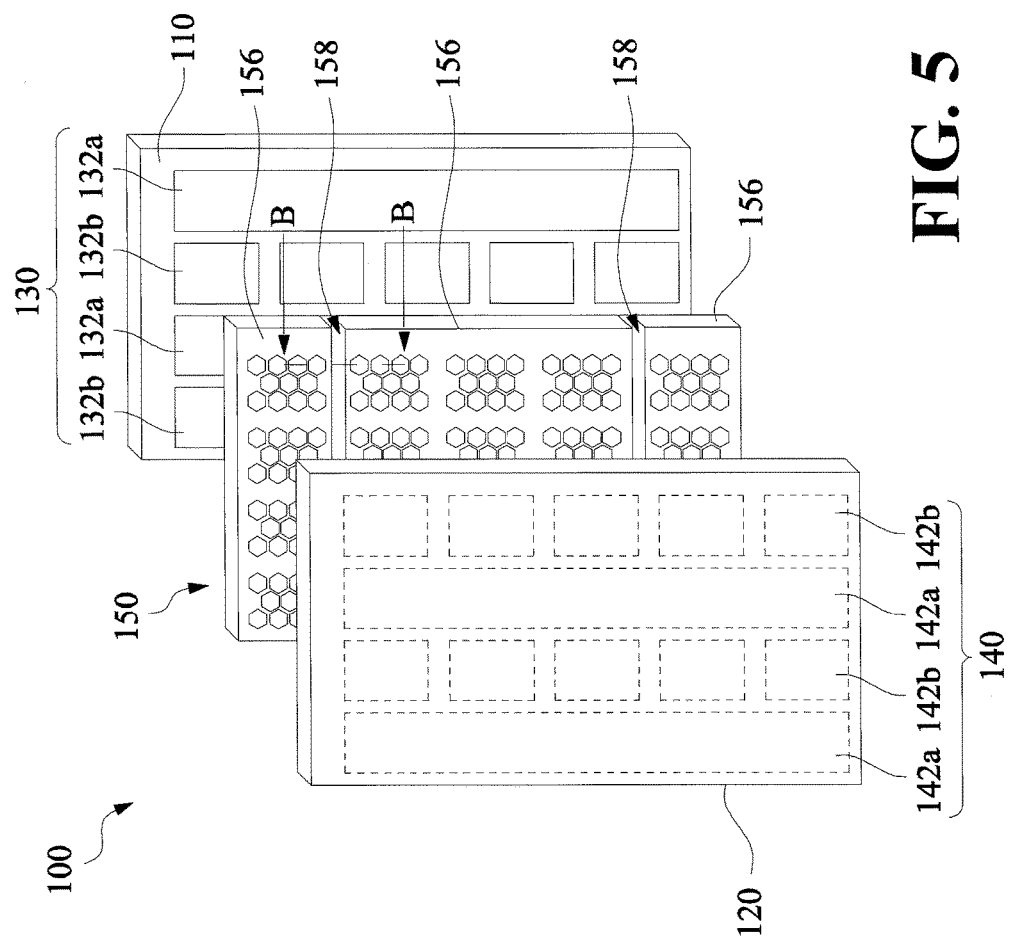
FIG. 5 shows a pressure sensing mat according to one or more embodiments of the present disclosure.

FIG. 5 shows a pressure sensing mat according to one or more embodiments of the present invention. The pressure sensing mat described with respect to FIG. 5 is substantially similar to that shown in FIG. 1. Accordingly, components and functions that have already been described will be omitted for the sake of brevity.

One difference between the pressure sensing mat shown in FIG. 1 and the pressure sensing mat shown in FIG. 5 is that the spacer layer 150 in FIG. 5 is divided into a plurality of spacer blocks 156 that are not connected to each other. For example, gaps 158 are designed to separate the plurality of blocks so that the blocks do not contact each other. Advantageously, in this configuration if a user folds the pressure sensing mat 100 for storage, the pressure sensing mat 100 can be folded along the gaps 158 to save space without damaging the electrode patterns.

Figure 6:
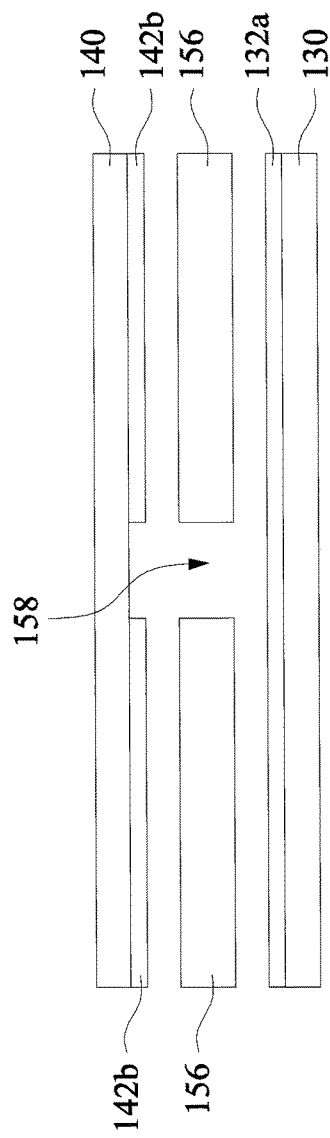
FIG. 6 shows a sectional view of the pressure sensing mat shown in FIG. 5 along line B-B.

FIG. 6 shows a sectional view of the pressure sensing mat shown in FIG. 5 along line B-B. The spacer blocks 156 are configured to contact the first electrode patterns 132*a*, 132*b* and the second electrode patterns 142*a*, 142*b*. The gaps 158 of the spacer layer 150 are disposed to coincide with the portions of the first substrate 110 and the second substrate 120 where at least one electrode pattern is not disposed. The gaps 158 are disposed in this manner so that, if a user folds the pressure sensing mat 100 along the gaps 158, the electrode patterns are not folded and damaged. To illustrate, as shown in FIG. 5, the gaps 158 are disposed to coincide with the portions of the second substrate 120 where at least one electrode pattern is not disposed.

Figure 7:
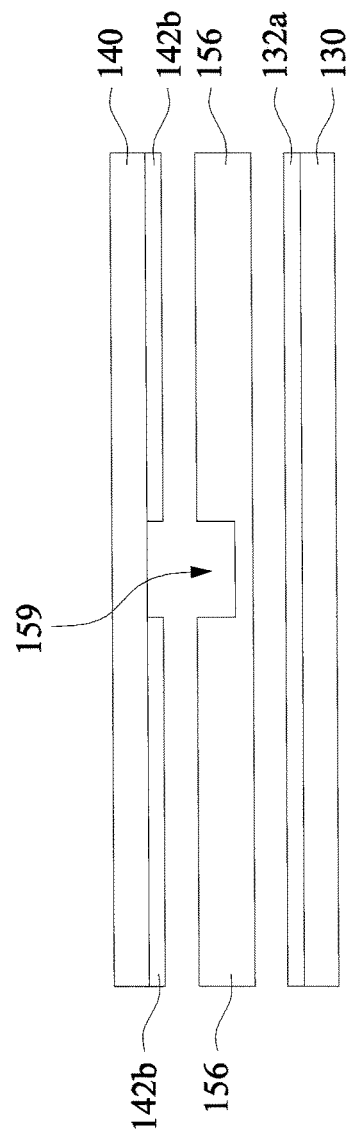
FIG. 7 shows an alternate embodiment of a sectional view of a pressure sensing mat shown in FIG. 5 along line B-B wherein the spacer layer has a groove instead of a gap.

FIG. 7 shows a sectional view of a pressure sensing mat according to one or more embodiments of the present invention and is similar to the pressure sensing mat shown in FIG. 6. Accordingly, components and functions that have already been described are omitted for the sake of brevity.

One of the differences between FIGS. 6 and 7 is that, although the spacer layer 150 in FIG. 7 is also divided into spacer blocks 156, the spacer blocks 156 of FIG. 7 remain connected to each other. In particular, the spacer layer 150 comprises grooves 159. Similarly, the grooves 159 of the spacer layer 150 are disposed to coincide with portions of the first substrate 110 or the second substrate 120 where at least one electrode pattern is not disposed. Advantageously, if a user folds the pressure sensing mat 100 for storage, the pressure sensing mat 100 can be folded along the grooves to save space without damaging the electrode patterns.

Figure 8:
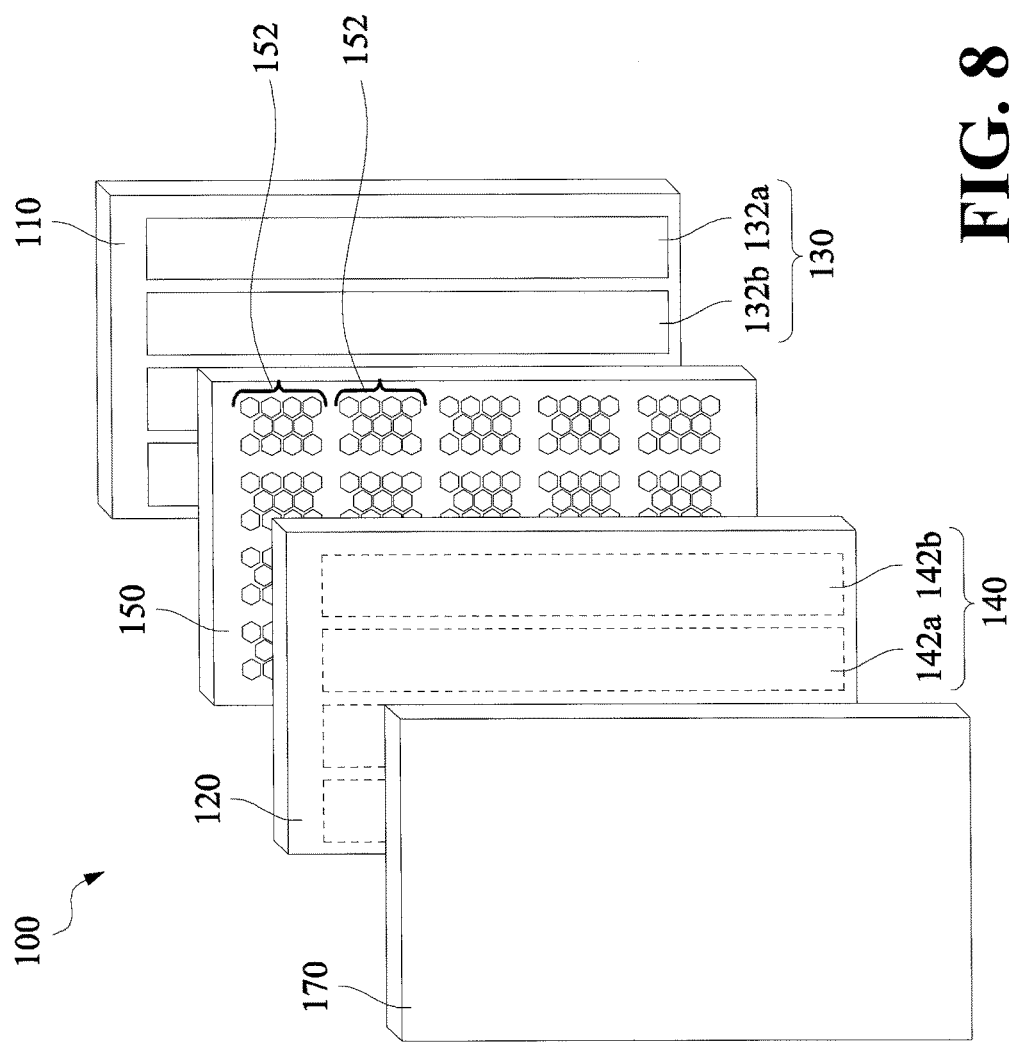
FIG. 8 shows a pressure sensing mat according to one or more embodiments of the present disclosure.

FIG. 8 shows a pressure sensing mat according to one or more embodiments of the present invention. The pressure sensing mat described with respect to FIG. 8 is substantially similar to that shown in FIG. 1. Accordingly, components and functions that have already been described will be omitted for the sake of brevity.

One of the differences between FIGS. 1 and 8 is that the pressure sensing mat 100 in FIG. 8 further comprises a third substrate 170. Specifically, in FIG. 8, the third substrate 170 is disposed on a side of the second substrate 120 opposite to the side that faces the first substrate 110. Both the second substrate 120 and the third substrate 170 may be made of the same or different flexible materials.

In one or more embodiments of the present invention, the material of the third substrate 170, in comparison to the material of the second substrate 120, may be better at reducing audible noise from the substrates and produce less noise due to deformation of the pressure sensing mat, whereas the material of the second substrate is the better of the two in preventing deformation or damage of the circuitry disposed thereon. Accordingly, in one or more embodiments of the present invention, the third substrate 170 may be disposed such that it is adjacent to the user to reduce audible noise due to movement, and the electrode patterns are disposed on the second substrate 120 to prevent the electrode patterns from being damaged. In one or more embodiments of the present invention, the second substrate 120 may be a polyethylene terephthalate (PET) film and the third substrate 170 may be a thermoplastic polyurethane (TPU) film.

Another difference between FIGS. 1 and 8 lies in the configuration of the electrode patterns. In FIG. 8, the first electrode patterns 132a, 132b and the second electrode patterns 142a, 142b are rectangular in shape. Specifically, each of the first electrode patterns 132a is disposed to coincide with each of the second electrode patterns 142b, and each of the second electrode patterns 132b is disposed to coincide with each of the second electrode patterns 142a.

Another difference between FIGS. 1 and 8 lies in the hole patterns 152 of the spacer layer 150. In FIG. 8, a plurality of hole patterns 152 are disposed to coincide with one first electrode pattern 132a, 132b. In this way, when the user exerts pressure on the pressure sensing mat 100, each of the first electrode patterns 132a, 132b may respectively contact their corresponding second electrode patterns 142b, 142a through the hole patterns 152, thereby increasing sensitivity.

Figure 9:
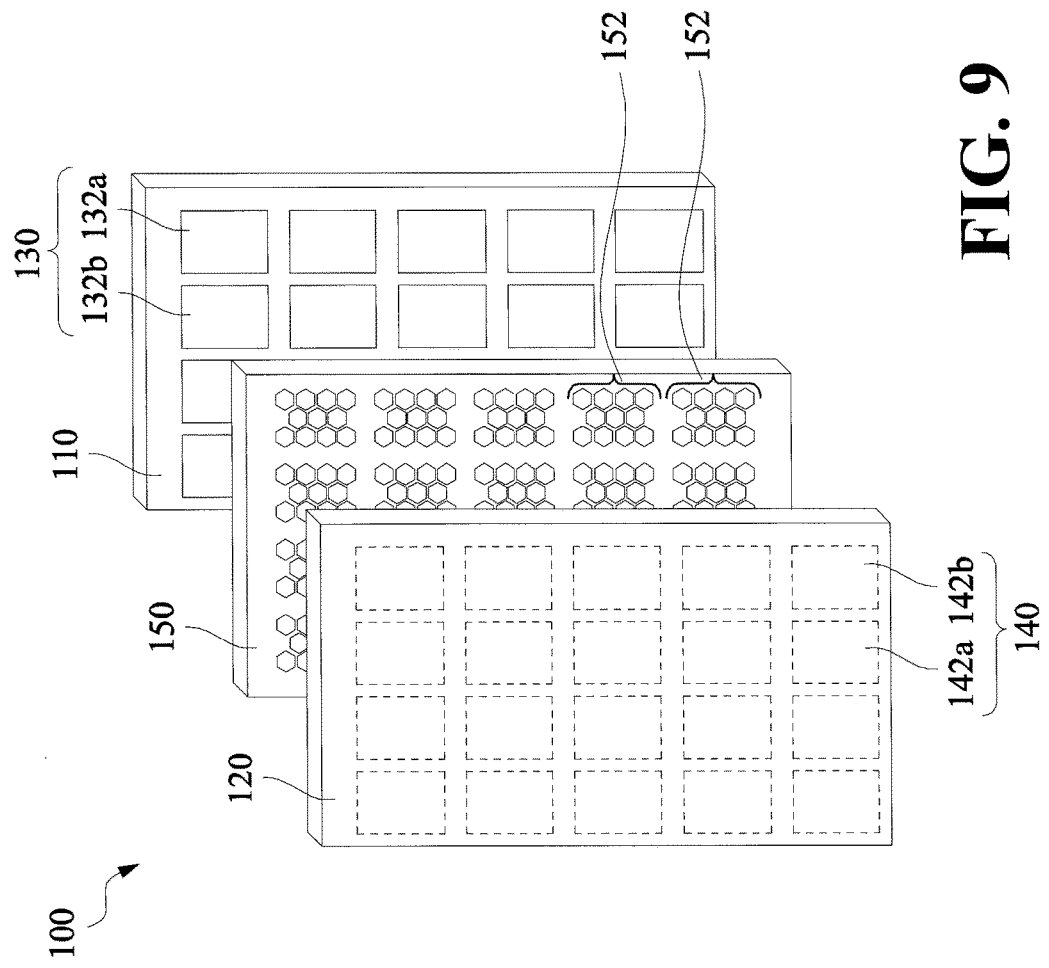
FIG. 9 shows a pressure sensing mat according to one or more embodiments of the present disclosure.

FIG. 9 shows a pressure sensing mat according to one or more embodiments of the present invention. The pressure sensing mat described with respect to FIG. 9 is substantially similar to that shown in FIG. 1. Accordingly, components and functions that have already been described will be omitted for the sake of brevity.

One of the differences between FIGS. 1 and 9 is that, in FIG. 9 the electrode patterns are all square shaped, and each of the first electrode patterns 132a is disposed to coincide with each of the corresponding second electrode patterns 142b, and each of the first electrode patterns 132b is disposed to coincide with each of the corresponding second electrode patterns 142a.

Applications of the Pressure Sensing Mat

The pressure sensing mat described above may be integrated into a mattress or mattress covering that would allow for the monitoring of a person laying thereon. For example, the pressure sensing mat may be crafted into a mattress so that a person laying thereon may have their breathing rhythm, heartbeat, pulse, movement/posture, etc. constantly monitored. In other embodiments, instead of integrating the pressure sensing mat into a standalone mattress a separate mattress covering with the pressure sensor mat therein may be applied to a preexisting mattress so that a person laying thereon may have their breathing rhythm, heartbeat, pulse, movement/posture, etc. constantly monitored.

Figure 10A:
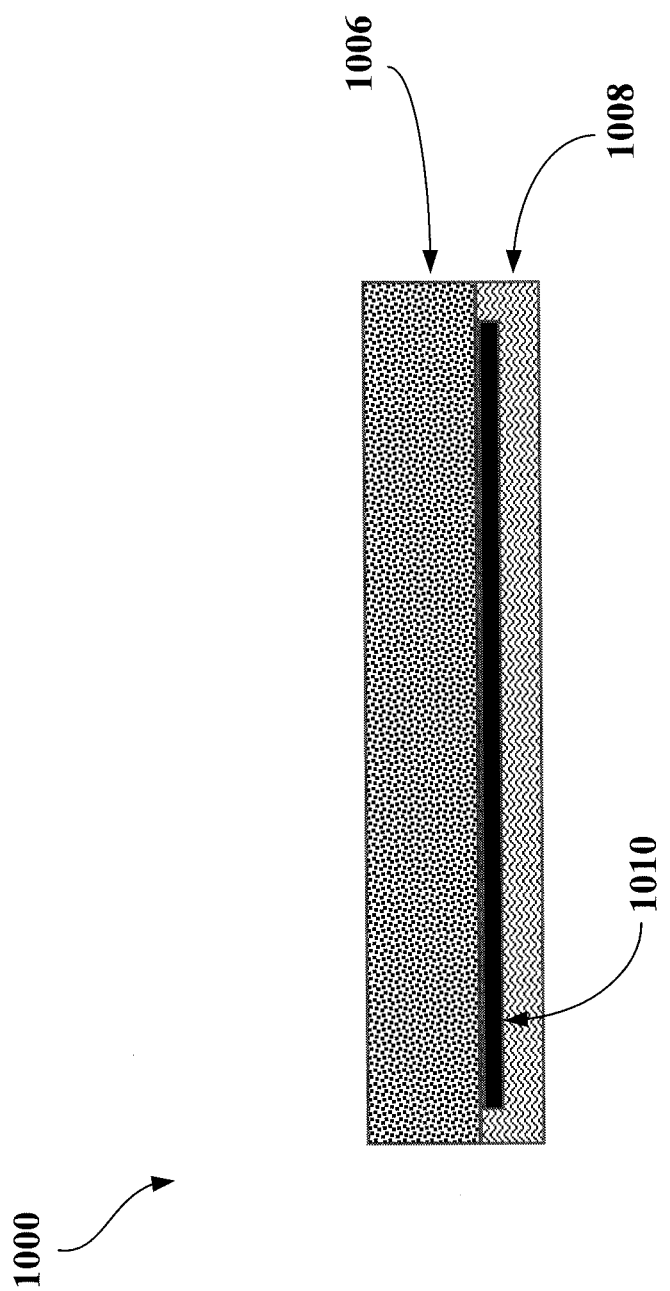
FIG. 10A shows a sectional view of a general embodiment for a mattress integrating a pressure sensing mat.

A sectional view of a general embodiment for a mattress integrating the pressure sensing mat is depicted in FIG. 10A. As can be seen in FIG. 10A, the mattress 1000 includes at least one upper layer 1006 and at least one lower layer 1008. Disposed in between the upper layer 1006 and the lower layer 1008 is a pressure sensing mat 1010. Each of the upper layer and the lower layer may be fabricated from a foamed plastic to ensure that the mattress 1000 is soft, deformable, and ultimately comfortable to the person lying thereon.

Figure 10B:
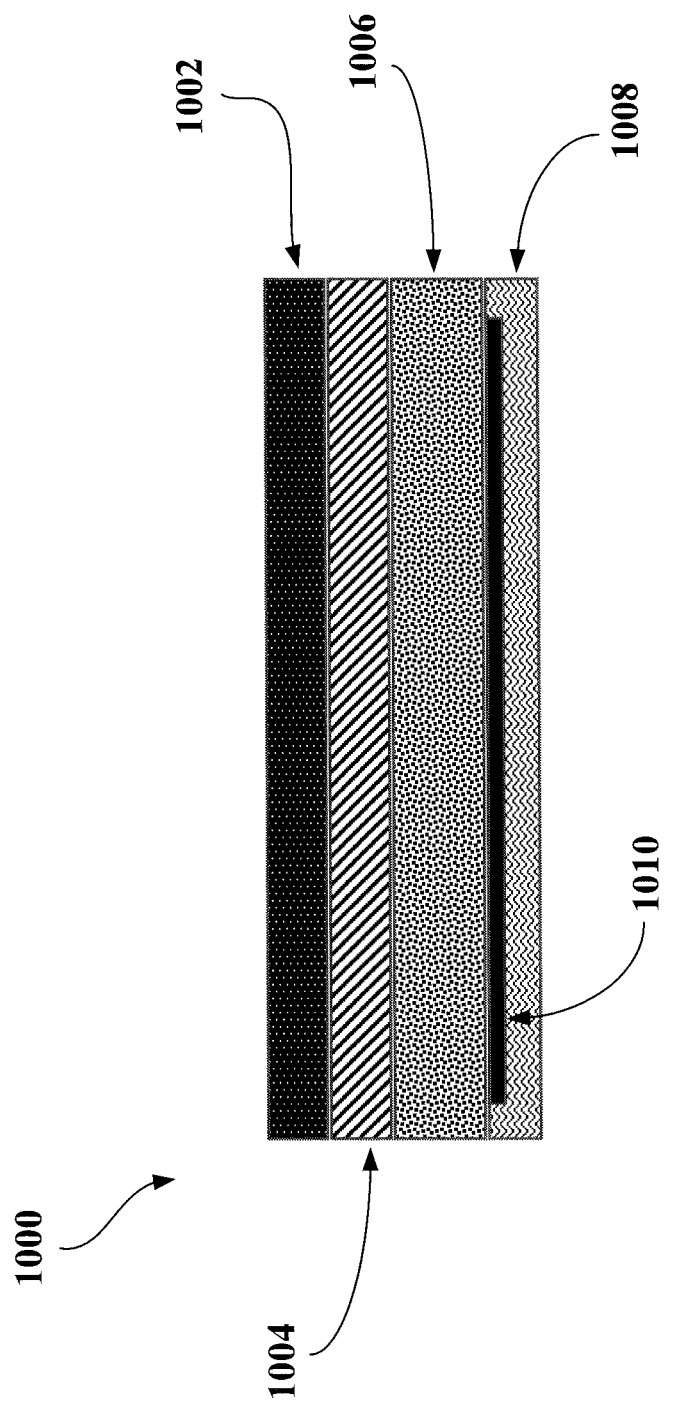
FIG. 10B shows a sectional view of one or more embodiments for a mattress integrating a pressure sensing mat.

A sectional view of one or more embodiments for a mattress integrating the pressure sensing mat is depicted in FIG. 10B. As can be seen in FIG. 10B, the mattress 1000 includes, from the uppermost layer to the lowermost layer, a first layer 1002, a second layer 1004, a third layer 1006, and a fourth layer 1008. Disposed in between the third and the fourth layers is a pressure sensing mat 1010. Each of the first through fourth layers may be fabricated from a foamed plastic to ensure that the mattress 1000 is soft, deformable, and ultimately comfortable to the person lying thereon. As discussed above, configurations of the mattress integrating the pressure sensing mat are not limited to those shown in FIGS. 10A and 10B. That is, one of ordinary skill in the art would appreciate that the number of the layer of the mattress 1000 and the placement of the pressure sensing mat between certain layers can vary without departing from the scope of the present invention.

In some embodiments, the pressure sensing mat 1010 may be sized and positioned within the mattress 1000 so that a person laying down upon the mattress would have their trunk and upper extremity (e.g., their shoulders through waist and through arms) exerting pressure on the pressure sensing mat 1010. In some embodiments, the pressure sensing mat 1010 may be sized and positioned within the mattress so that a person laying down upon the mattress would have their trunk and lower extremity (e.g., their thighs through feet) exerting pressure on the pressure sensing mat. Further, in some embodiments a pressure sensing mat may be specifically sized to generally accommodate an infant, toddler, juvenile, young adult, or adult of either gender.

Figure 11:
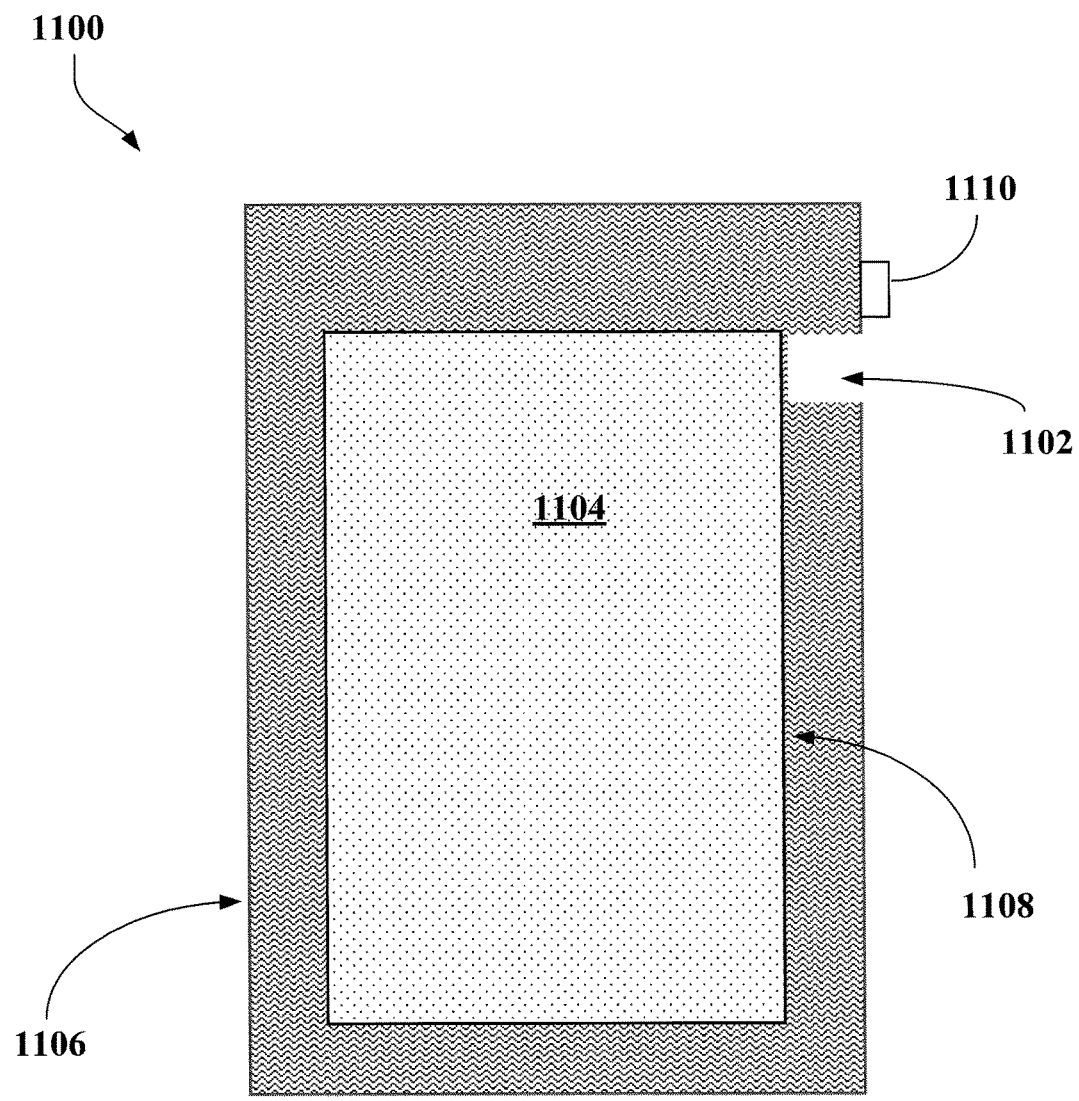
FIG. 11 shows a top view of a general embodiment for the mattress integrating a pressure sensing mat

A top view of a general embodiment for the mattress integrating the pressure sensing mat is depicted in FIG. 11. The view depicts the outer edge 1106 of the lowermost layer of the mattress, with the upper layer(s) omitted for clarity. The pressure sensing mat 1104 is placed upon the upper side of the lowermost layer of the mattress 1100 which may be adjacent to the bottom side of the upper layer of the mattress 1100. In some embodiments, a portion of the lowermost layer may be cut out in order to accommodate the placement of the pressure sensing mat 1104 thereon so that the layering may remain level. There may be an outlet 1102 created in the mattress 1100, and this outlet may be where the main wires of the pressure sensing mat may be operatively connected to a processor 1110 and/or other data collection and transmission apparatuses (e.g., Bluetooth® or other wireless transmission/receiving devices) outside the mattress. The processor 1110 may be integrated circuit, such as microcontroller, digital signal processor, application specific integrated circuit, or logic circuit. The positioning of the outlet is not intended to be limited by its positioning in FIG. 11, and the outlet 1102 may be placed anywhere in the mattress 1100 that is convenient to provide access for connecting the wires of the pressure sensing mat to the processor and/or other data collection and transmission apparatuses. Importantly, in some embodiments, the processor connected to the pressure sensing mat may work in conjunction with the Bluetooth® standard or other wireless transmission protocols to wirelessly transmit, receive, and/or record the data collected from a person lying on the mat to a central computer for analysis.

In one or more embodiments, the mattress may be configured to facilitate the replacement of the pressure sensing mat in the event that a new patient occupies the mattress or in the event of its failure due to either damage or a deterioration in its sensing capabilities. In this configuration a cutout may be made within the lowermost layer of the mattress. This cutout may completely separate the lowermost layer into an outer perimeter portion and a cutout portion. The dimensions of the cutout may be slightly larger or substantially the same as the peripheral edge 1108 defining the boundaries of the pressure sensing mat 1104 and the outlet 1102 shown in FIG. 11. This cutout may then serve as a platform to dispose the pressure sensing mat, whereby the pressure sensing mat is attached thereon or is placed within a pouch or other case attached to the cutout/platform. Upon, securing the pressure sensing mat to the cutout/platform of the lowermost layer, the cutout may be returned to its location in the mattress so that the pressure sensing mat is disposed between the lowermost layer and the upper layer adjacent to the lowermost layer as depicted in FIG. 10A or the third layer and the forth layer as depicted in FIG. 10B.

Thus, to exchange the pressure sensing mat, one just has to lift the mattress and remove the cutout/platform located in the bottommost layer that has either the mat or the pouch containing the mat attached thereto. A new pressure sensing mat may then be secured upon the cutout/platform or be placed in the poach attached to the cutout/platform. Then the cutout/platform may be returned to its position within the mattress. In some embodiments, the pressure sensing mat may be disconnected from the processor or other data collection and transmission apparatus via the outlet prior to or during the exchange and suitable connected to the processor or other data collection and transmission apparatus via the outlet after the exchange.

In some embodiments, the pouch or other case to place the pressure sensing mat therein may be formed from a cloth or plastic material that may then be glued or otherwise attached to the cutout platform. Specifically, the pouch may be fabricated from TPU, PET, cotton, cotton/synthetic blends, etc. Further, in order to secure the pressure sensing mat therein, the pouch or other case may include a zipper or other closure to restrict the migration of the pressure sensing mat when in use within the mattress.

The mattress covering may possess a similar structure to that of the mattress with fewer foam layers in order to decrease the thickness of the covering so that the mattress covering may provide a comfortable surface for laying. Further, in some embodiments the mattress covering (including the pressure sensing mat) may be substantially the same dimensions of the mattress that it is to be set upon. In other embodiments, the covering (including the pressure sensing mat) may be sized to substantially accommodate only a particular portion of a person, for example a person's trunk (e.g., their shoulders through waist).

In use within a standalone mattress, mattress covering or other application, the pressure sensing mat may use thermoplastic polyurethane (TPU) or polyethylene terephthalate (PET) for the first and/or second substrate. The use of TPU may be preferred due to its ability to be fabricated as a softer, more flexible, and thinner material, which may increase the comfort for the person using the mat. The use of PET as a substrate material may be preferred due to its relative sturdiness and capability of reliably supporting the electrode circuitry printed and applied thereon.

In use within a standalone mattress, mattress covering, or other application when sufficient pressure is exerted on the pressure sensing mat, the electrodes applied on opposing faces of the first and second substrates contact each other via the holes within the spacer layer to form a complete circuit. The pressure sensing mat may detect the position of contact of the electrodes on the mat to determine the location of the source of the pressure. As mentioned above, the size of the holes within the spacer layer may be adjusted based on their positioning on the pressure sensing mat to account for the positioning of a person upon the mat. Generally, larger holes in the spacer layer require less pressure input to contact the opposing electrodes and register a signal. Therefore, larger holes may be best suited to be positioned in the areas of a pressure sensing mat where smaller and less massive body areas will be laying thereon.

For example, the shoulders, waist and feet are some of the heavier components of the human body. Thus, those body areas will exert more pressure on the pressure sensing mat when a person lies on a mattress or mattress covering having the pressure sensing mat therein. Consequently, the spacer layer of the pressure sensing mat in the regions supporting these body areas do not need as large of holes therein comparing other body areas. In general, to increase the sensitivity of the pressure sensing mat monitoring body areas with less mass, the holes in the spacer layer should be made larger, and vice-versa. As an example, the portion of the spacer layer where the waist/hips are most likely to be disposed will have smaller sized holes than the portion of the spacer layer where the feet are most likely to be disposed. Further, the portion of the spacer layer where the shoulders are most likely to be disposed may have holes that are sized between the waist/hip and feet areas.

In one or more embodiments, another pressure sensing device may be used in conjunction with the pressure sensing mat in order to measure the breathing rhythm of a person. While the pressure sensing mat may be capable of measuring the breathing rhythm on its own (due to the movement of a person's trunk while exhaling and inhaling), the measurement of the breathing rhythm may be more accurate when utilizing a separate pressure sensing device for this purpose. The separate pressure sensing device may be disposed on the upper surface of the pressure sensing mat that is closest to the subject being tested.

In one or more embodiments, the separate pressure sensing device may include at least one piezoelectric sensing module to detect a person's breathing rhythm. In one or more embodiments, the piezoelectric sensing module comprises at least one layer made from one of TPU, PET, Mylar, foamed plastics, natural or synthetic sponge and a piezoelectric material adjacent thereto. In other embodiments, the piezoelectric sensing module comprises a plurality of layers each of which may be fabricated from one of TPU, PET, Mylar, foamed plastics, natural or synthetic sponge, silicone rubber, etc. and a piezoelectric material may be disposed between any of two layers of the piezoelectric sensing module.

Figure 13A:
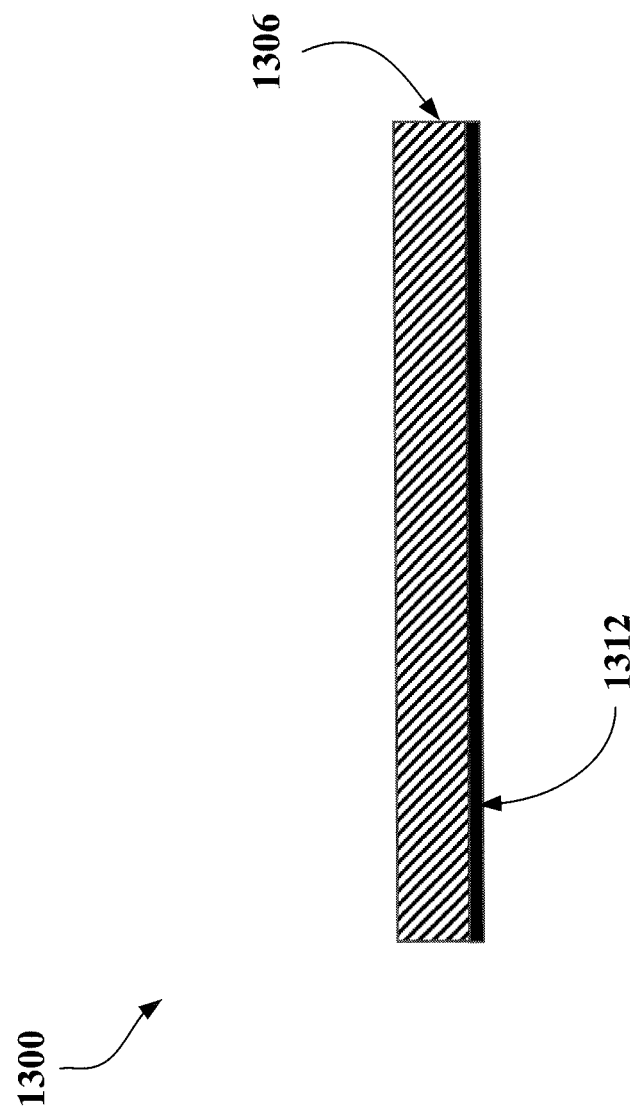
FIG. 13A shows a sectional view of an embodiment of a separate pressure sensing device.
Figure 13B:
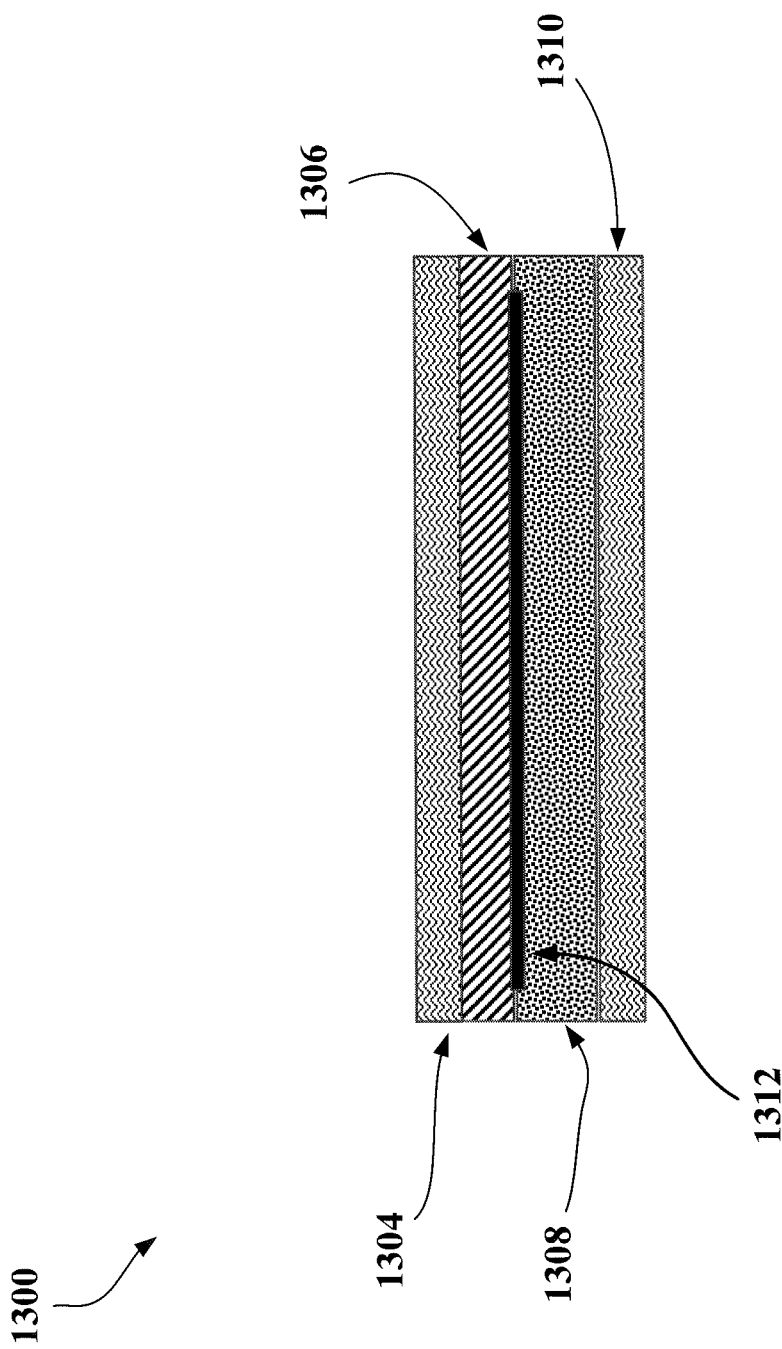
FIG. 13B shows a sectional view of another embodiment of a separate pressure sensing device.

FIGS. 13A and 13B depict embodiments of the piezoelectric sensing module to detect a person's breathing rhythm. In one or more embodiments, FIG. 13A depicts a side perspective view of a piezoelectric sensing module 1300 including a deformable layer 1306 and a piezoelectric material 1312. The deformable layer 1306 may be made from one of TPU, PET, Mylar, foamed plastics, natural or synthetic sponge, silicone rubber, etc. In one or more embodiments, the piezoelectric material 1312 is adjacent to the pressure sensing mat. FIG. 13B depicts a side perspective view of a piezoelectric sensing module 1300 with the top to bottom layers including a first layer 1304, a second layer 1306, a piezoelectric material 1312, a third layer 1308, and a fourth layer 1310. The fourth layer 1310 is the layer that is proximate and adjacent to the pressure sensing mat. Each of the first through fourth layers may be fabricated from one of TPU, PET, Mylar, foamed plastics, natural or synthetic sponge, silicone rubber, etc. One of ordinary skill in the art would appreciate that although various layers are shown in the figures as well as the location of the piezoelectric material to be disposed, the actual position, number, size, etc. of the layers and the piezoelectric material can vary without departing from the scope of the present invention.

In some embodiments, the piezoelectric material may be a piezoelectric film. When force is exerted on the piezoelectric material, a voltage will appear across its opposite faces. For example, when the piezoelectric material is acted upon by the pressure exerted from a person's chest movement by breathing, the deformation/vibration of the piezoelectric material may generate real-time changes of potential difference. By way of deformation or vibration, the piezoelectric material may produce a certain degree of output voltage as well as a signal corresponding to the magnitude of the output voltage.

In one or more embodiments, when a person is lying on the piezoelectric material and breathing, deformation or vibration of the piezoelectric material may occur corresponding to the person's breathing rhythm. The larger the degree of deformation/vibration, the higher the output voltage. Accordingly, the signal corresponding to the output voltage generated from deformation/vibration of the piezoelectric material may contain information relating to the person's breathing. Such signal may be a signal voltage level, a current value, a pulse signal or various other electrical signals.

Since the piezoelectric material is relatively soft, it has high sensitivity for sensing pressure. It may be particularly beneficial to the sensitivity of the piezoelectric material 1312 and the accuracy of signal detection if at least one layer above the piezoelectric material 1312 was made of a harder plastic than the piezoelectric material and/or any of the other layers, such as TPU, and at least one layer below the piezoelectric material 1312 was made of softer materials than any of other layers, such as synthetic or natural sponge, foamed plastics, and combinations thereof.

For accurate measurements of a person's breathing rhythm, the separate pressure sensing device may be placed on and adhered to the pressure sensing mat at roughly the position that would be expected for a person's chest or trunk to rest. The piezoelectric material positioned in this way may be able to detect the movement of a person's chest to determine their breathing rhythm. However, the movement of a person's chest associated with their breathing is variable depending upon their sleeping position (e.g., flat on back, flat on front, on side, etc.). In some embodiments, the pressure sensing mat may serve to detect a person's posture while the gain of the piezoelectric circuit within the separate pressure sensing device is adjusted via a pre-programmed algorithm or filter circuit in conjunction with the person's posture detected in order to obtain an adequate signal for breathing rhythm determination. Once a sufficient amount of data is collected on a person's breathing rhythm it may be possible to determine certain breathing patterns. While these breathing patterns may be analyzed by a trained practitioner, an algorithm may be developed that can be used to indicate or diagnose patterns related to certain diseases or harmful breathing situations (e.g., sleep apnea, asthma, coughing, etc.).

Figure 12:
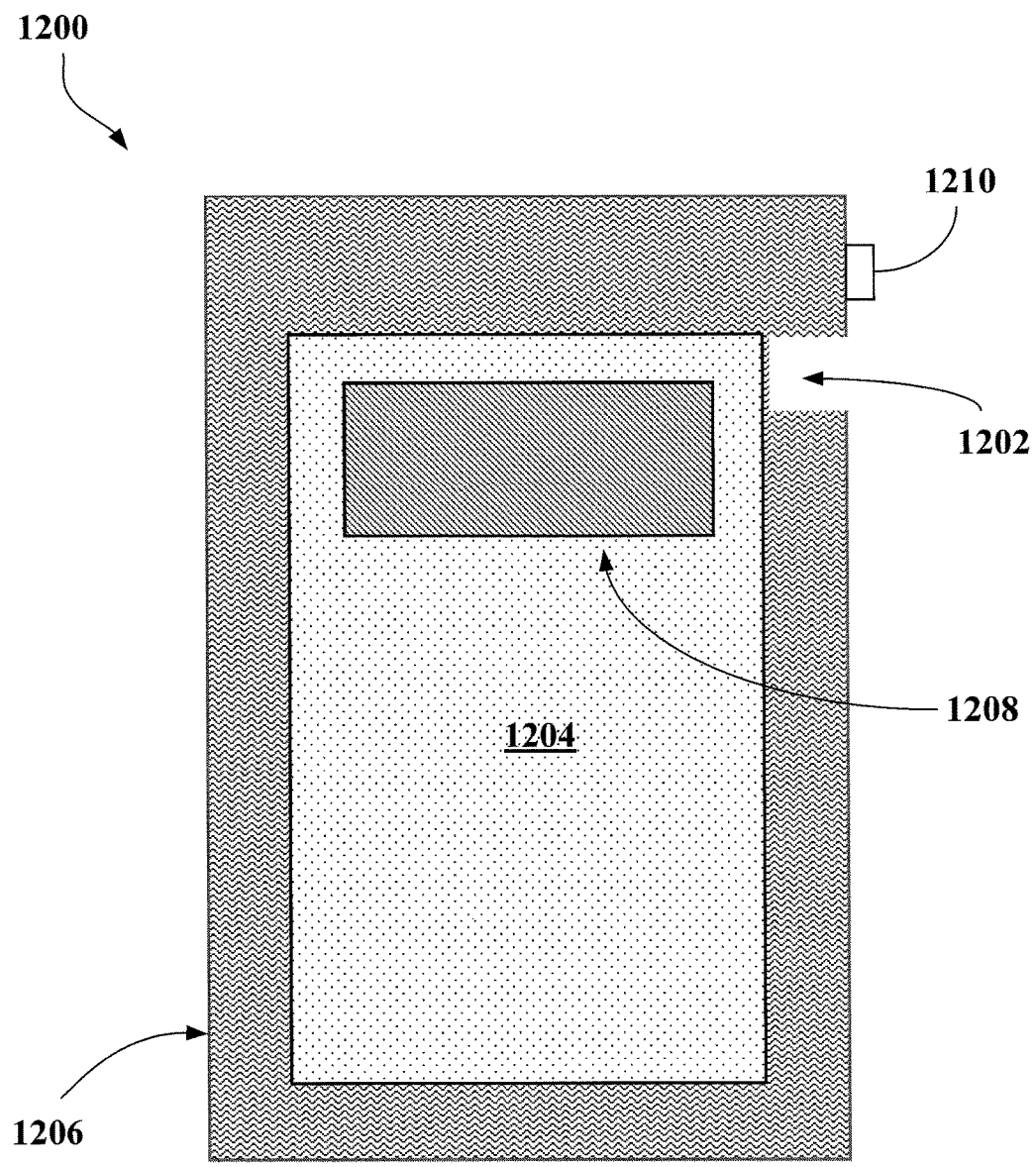
FIG. 12 shows an embodiment depicting the placement of a separate pressure sensing device on a pressure sensing mat within a mattress or mattress covering.

FIG. 12 depicts one of the embodiments showing the placement of a separate pressure sensing device 1208 on a pressure sensing mat 1204 within a mattress or mattress covering 1200. Similarly to FIG. 11, the upper layer(s) of the mattress is omitted for clarity, and the lowermost layer 1206 of the mattress with a pressure sensing devices thereon is shown. The outlet 1202 may serve to facilitate the connection of the separate pressure sensing device 1208 and the pressure sensing mat 1204 to the processor 1210 or other data collection and transmission apparatuses (e.g., Bluetooth® or other wireless transmission/receiving devices). The separate pressure sensing device may be operatively connected to the same processor as the pressure sensing mat for ease of data collection and transmission. The processor 1210 may be an integrated circuit, such as microcontroller, digital signal processor, application specific integrated circuit, or logic circuit. The positioning of the outlet is not intended to be limited by its positioning in FIG. 12, and the outlet 1202 may be placed anywhere in the mattress 1200 that is convenient to provide access for connecting the wires of the pressure sensing mat and the separate pressure sensing device to the processor and/or other data collection and transmission apparatuses. Importantly, in some embodiments, the processor connected to the pressure sensing mat and the separate pressure sensing device may work in conjunction with the Bluetooth® standard or other wireless transmission protocols to wirelessly transmit, receive, and/or record the data collected from a person lying on the mat and the separate sensing device to a central computer for analysis.

Figure 14:
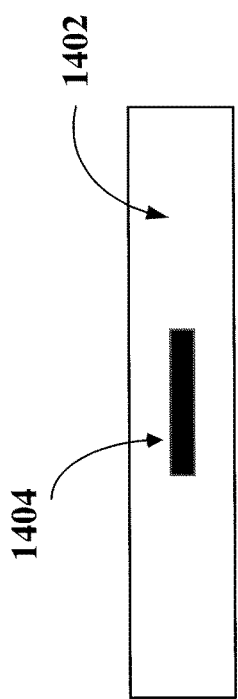
FIG. 14 shows a top view of an embodiment of a separate pressure sensing device.
Figure 15:
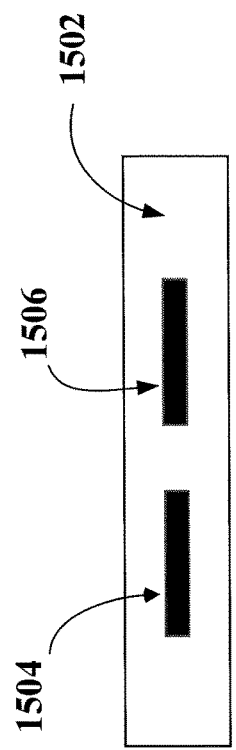
FIG. 15 shows a top view of an embodiment of a separate pressure sensing device.

FIGS. 14-15 depict a top view of a piezoelectric module of a separate pressure sensing device. For the sake of clarity, the layers above the piezoelectric materials are not shown. In FIG. 14 a material layer 1402 supports a single piezoelectric material 1404. In FIG. 15 a material layer 1502 supports two piezoelectric materials 1502 and 1504. Generally, more (in number or in size) piezoelectric materials will render a more sensitive sensor. Additionally, while the piezoelectric module of the separate pressure sensing device may be positioned to be perpendicular to the orientation of a person laying upon the device, the application is not so limited. For example, the piezoelectric module of the separate pressure sensing device may be at any angle to the orientation of a person laying upon the device, and in some embodiments a separate pressure sensing device may include two piezoelectric modules criss-crossed (e.g., forming an X-shape) in order to provide a larger measuring area.

Figure 16:
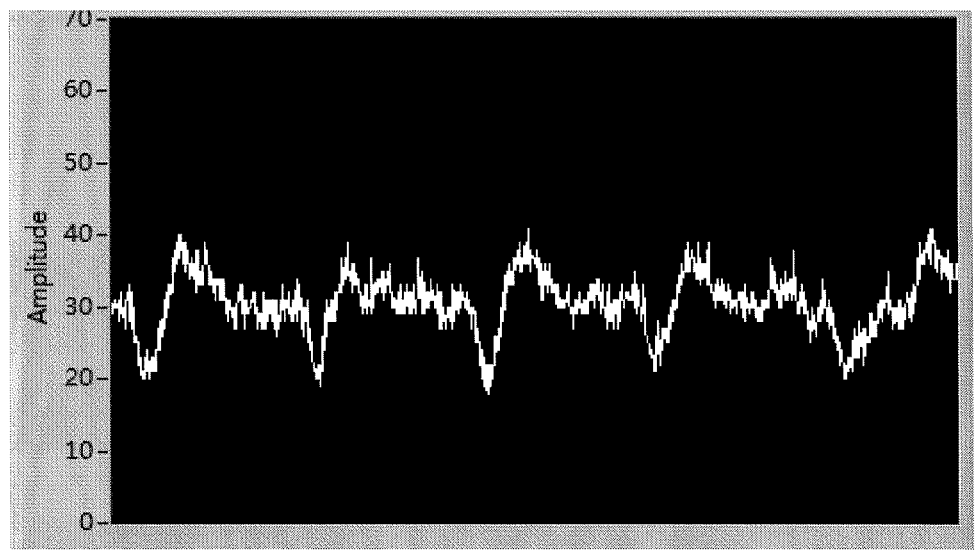
FIG. 16 shows experimental signals collected by a separate pressure sensing device according to FIG. 14 with a subject lying flat on their back
Figure 17:
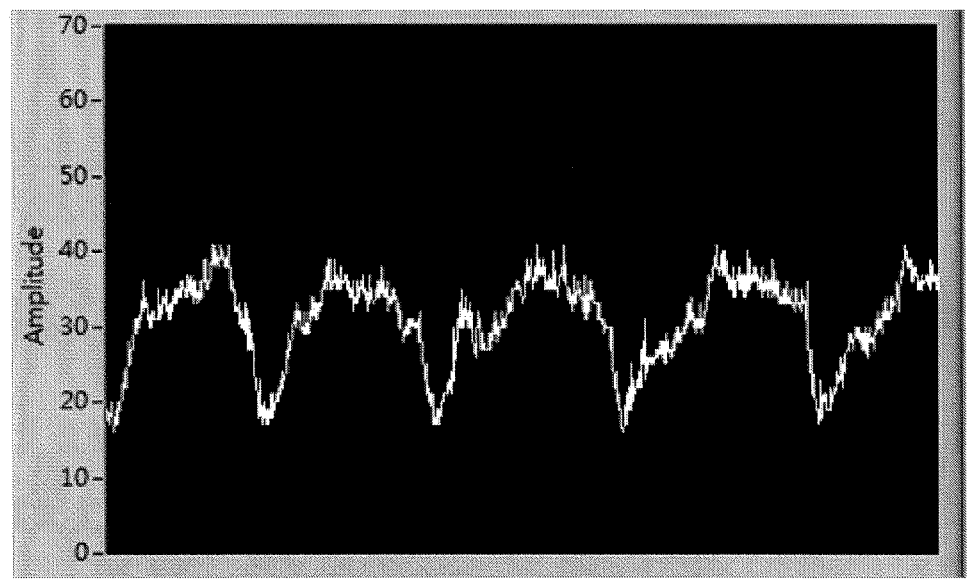
FIG. 17 shows experimental signals collected by a separate pressure sensing device according to FIG. 15 with a subject lying flat on their back.
Figure 18:
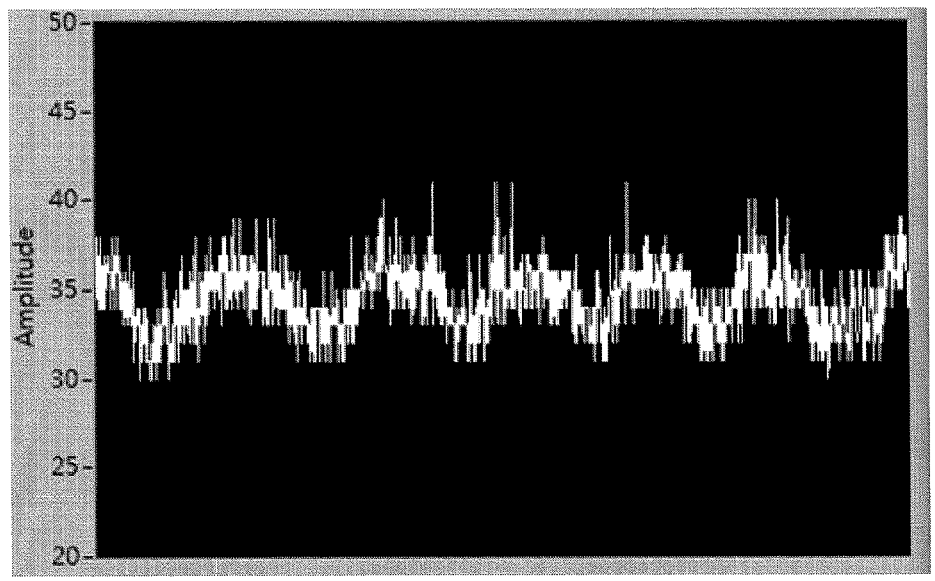
FIG. 18 shows experimental signals collected by a separate pressure sensing device according to FIG. 14 with a subject lying on their side on the right side of a mattress (when viewed from the foot of the mattress).
Figure 19:
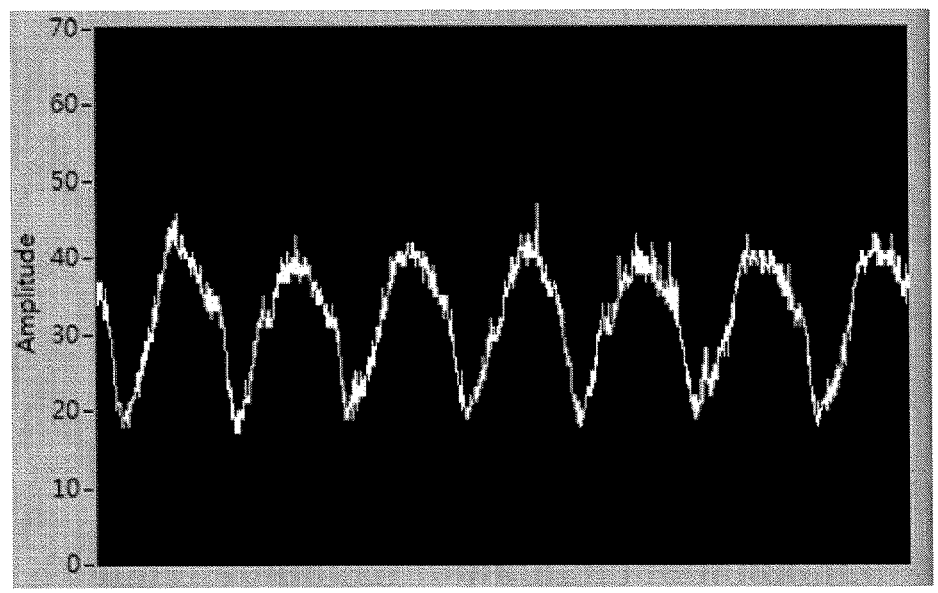
FIG. 19 shows experimental signals collected by a separate pressure sensing device according to FIG. 15 with a subject lying on their side on the right side of a mattress (when viewed from the foot of the mattress).

FIGS. 16-19 demonstrate the effect of the positioning of the piezoelectric materials, the amount of piezoelectric materials present in a piezoelectric module of a separate pressure sensing device, and the location of the subject being tested have on the quality of the measurement obtained. In each test a piezoelectric sensor according to either FIG. 14 or 15 was positioned in the middle of a mattress below the pillow and adjacent to the subject's chest or trunk. FIGS. 16 and 17 depict experimental signals collected by a separate pressure sensing device according to FIGS. 14 and 15, respectively, with a subject lying flat on their back in the middle of the mattress. In each case the experimental data is adequate to determine a breathing rhythm and there is not substantial variation between the data. FIGS. 18 and 19 depict experimental signals collected by a separate pressure sensing device according to FIGS. 14 and 15, respectively, with a subject lying on their side on the right side of a mattress (when viewed from the foot of the mattress). The experimental data acquired in FIG. 19 (with a separate pressure sensing device utilizing two piezoelectric materials) provides much sharper resolution of the breathing rhythm of the subject and thus would be much more amenable to analysis.

Figure 20:
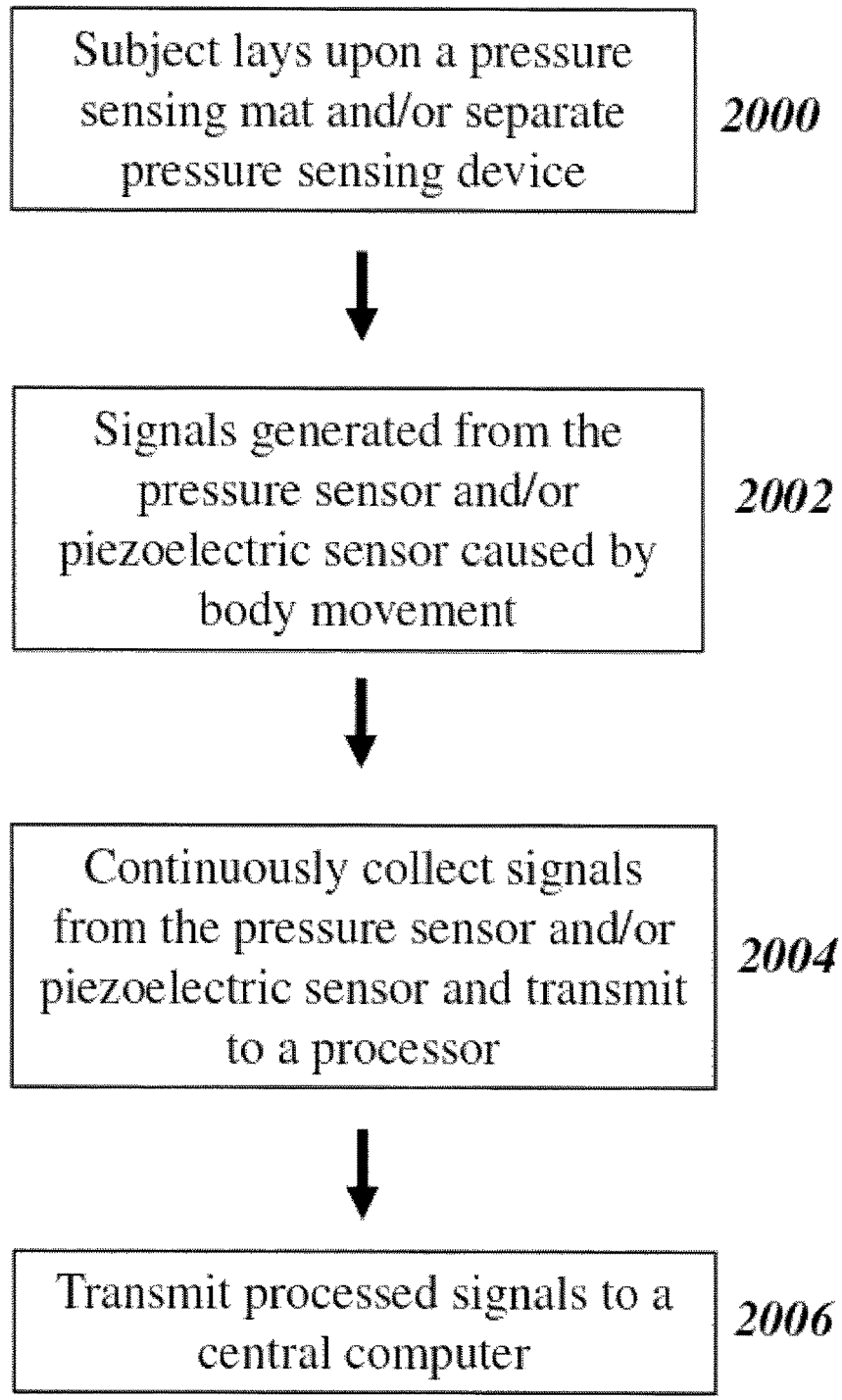
FIG. 20 shows a general flowchart for the monitoring of a subject according to some embodiments.

A general flowchart for the monitoring of a subject according to some embodiments may be found in FIG. 20. In the method a subject may lay down upon a pressure sensing mat (directly or indirectly) and/or a separate pressure sensing device including at least one piezoelectric module, signals may be generated from the pressure sensing mat and/or the separate pressure sensing device due to the subject's body movement 2002, the signals generated may be continuously collected and transmitted to a processor 2004, and the processed signals may be transmitted to a central computer for further data processing and/or analysis 2006.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A pressure sensing mat comprising:
a first substrate;
a second substrate disposed opposite to the first substrate;
a first electrode layer disposed on a side of the first substrate that faces the second substrate, the first electrode layer comprising a plurality of first electrode patterns;
a second electrode layer disposed on a side of the second substrate that faces the first substrate, the second electrode layer comprising a plurality of second electrode patterns; and
a spacer layer disposed between the first substrate and the second substrate and comprising a plurality of hole patterns such that the first electrode patterns are configured to contact the second electrode patterns through the plurality of hole patterns,
wherein each of the hole patterns comprises a plurality of holes and is disposed to coincide with a corresponding portion of the first electrode patterns, and
wherein the plurality of holes in a first hole pattern of the plurality of hole patterns comprise a larger hole size and a smaller number of holes than the plurality of holes in a second hole pattern of the plurality of hole patterns.

2. The pressure sensing mat according to claim 1, wherein the first substrate and the second substrate are flexible.

3. The pressure sensing mat according to claim 1, wherein the spacer layer is flexible, deformable, and made from an insulating material.

4. The pressure sensing mat according to claim 1, wherein the first hole pattern and the second hole pattern have different hole sizes in relation to a relative amount of pressure to be exerted by a corresponding body portion of a user in contact with the pressure sensing mat.

5. The pressure sensing mat according to claim 1, wherein:
each of the first substrate and the second substrate comprises a plurality of grounding areas and a plurality of conducting areas;
each of the first electrode patterns and the second electrode patterns comprises a plurality of grounding electrodes and a plurality of conducting electrodes; and
the grounding electrodes are disposed in the grounding areas and the conducting electrodes are disposed in the conducting areas.

6. The pressure sensing mat according to claim 1, wherein:
each of the first substrate and the second substrate comprises a plurality of openings within the substrate,
the plurality of openings are defined by an outline pattern separate from the first electrode layer and the second electrode layer, and
the plurality of openings are configured to reduce audible noise of user movement.

7. The pressure sensing mat according to claim 1, wherein:
at least one positioning index is disposed on the first substrate;
at least one positioning index is disposed on the second substrate;
at least one positioning hole is disposed on the spacer layer; and
the at least one positioning index on the first substrate and the at least one positioning index on the second substrate are configured to align with the at least one positioning hole on the spacer layer and connect to each other through the at least one positioning hole.

8. The pressure sensing mat according to claim 1, wherein each of the first substrate and the second substrate comprises a plurality of separation slots within the substrate,
wherein the plurality of separation slots are defined by an outline pattern separate from the first electrode layer and the second electrode layer, and
wherein the plurality of separation slots are configured to reduce audible noise of user movement.

9. The pressure sensing mat according to claim 1, wherein:
at least one of the first electrode layer and the second electrode layer further comprises an electric wire.

10. The pressure sensing mat according to claim 9, wherein the electric wire comprises:
a small area conducting layer; and
a large area conducting layer disposed on and adhered to the small area conducting layer;
wherein the large area conducting layer covers the small area conducting layer; and
a material of the large area conducting layer is different from a material of the small area conducting layer.

11. The pressure sensing mat according to claim 9, wherein a conductivity of the small area conducting layer is greater than a conductivity of the large area conducting layer.

12. The pressure sensing mat according to claim 9, wherein the material of the large area conducting layer is a conductive ink and the material of the small area conducting layer is a conductive metal.

13. The pressure sensing mat according to claim 1, wherein:
the spacer layer comprises a plurality of hole patterns, and
each of the hole patterns comprises a plurality of holes and is disposed to coincide with only one of the first electrode patterns.

14. The pressure sensing mat according to claim 1, wherein each of the first electrode patterns is disposed to coincide with a corresponding second electrode pattern.

15. The pressure sensing mat according to claim 1, wherein a portion of the first electrode patterns is disposed to coincide with only one of the second electrode patterns and a portion of the second electrode patterns is disposed to coincide with only one of the first electrode patterns.

16. The pressure sensing mat according to claim 1, wherein the first substrate and the second substrate is made from a material selected from the group consisting of thermoplastic polyurethane (TPU), polyethylene terephthalate (PET), cotton, flax wool, ramie, silk, leather and fur.

17. The pressure sensing mat according to claim 1, further comprising a processor, wherein each of the first electrode layers and the second electrode layers are operatively connected to the processor.

18. The pressure sensing mat according to claim 1, further comprising a third substrate disposed on the opposite side of the second substrate that faces the first substrate.

19. The pressure sensing mat according to claim 18, wherein the second substrate is a polyethylene terephthalate (PET) film and the third substrate is a thermoplastic polyurethane (TPU) film.

20. The pressure sensing mat according to claim 1, wherein the holes are at least one selected from a group consisting of hexagonal, square, and circular in shape.

21. The pressure sensing mat according to claim 1, wherein:
- the spacer layer is divided into a plurality of spacer layer blocks, and
- the spacer layer blocks are separated from each other.

22. The pressure sensing mat according to claim 1, wherein:
- the spacer layer is divided into a plurality of spacer layer blocks, and
- the spacer layer blocks are connected to each other via grooves.

23. The pressure sensing mat according to claim 1, wherein the holes of a portion of the spacer layer are larger in size than the holes of another portion of the spacer layer.

* * * * *